United States Patent
Kim et al.

(10) Patent No.: US 12,371,492 B2
(45) Date of Patent: Jul. 29, 2025

(54) HUMANIZED ANTIBODY SPECIFIC FOR CD22 AND CHIMERIC ANTIGEN RECEPTOR USING THE SAME

(71) Applicant: InnoBation Bio Co., Ltd., Seoul (KR)

(72) Inventors: Seung Koo Kim, Yongin-si (KR); Ki Tae Kim, Seoul (KR)

(73) Assignee: INNOBATION BIO CO., LTD., Seoul (KR)

( * ) Notice: Subject to any disclaimer, the term of this patent is extended or adjusted under 35 U.S.C. 154(b) by 216 days.

(21) Appl. No.: 18/337,875

(22) Filed: Jun. 20, 2023

(65) Prior Publication Data

US 2023/0365686 A1   Nov. 16, 2023

Related U.S. Application Data

(62) Division of application No. 17/563,846, filed on Dec. 28, 2021.

(30) Foreign Application Priority Data

Dec. 30, 2020  (KR) .................. 10-2020-0187510
Jun. 1, 2021   (KR) .................. 10-2021-0070934

(51) Int. Cl.
| | |
|---|---|
| C07K 16/28 | (2006.01) |
| A61K 39/00 | (2006.01) |
| A61K 39/395 | (2006.01) |
| A61K 40/11 | (2025.01) |
| A61K 40/31 | (2025.01) |
| A61K 40/42 | (2025.01) |
| C07K 14/705 | (2006.01) |
| C07K 14/725 | (2006.01) |
| C07K 16/30 | (2006.01) |
| C12N 5/0783 | (2010.01) |
| C12N 5/10 | (2006.01) |

(52) U.S. Cl.
CPC .. *C07K 16/2803* (2013.01); *A61K 39/001112* (2018.08); *A61K 39/001113* (2018.08); *A61K 39/3955* (2013.01); *A61K 39/39558* (2013.01); *A61K 40/11* (2025.01); *A61K 40/31* (2025.01); *A61K 40/4211* (2025.01); *A61K 40/4212* (2025.01); *C07K 14/7051* (2013.01); *C07K 14/70517* (2013.01); *C07K 14/70578* (2013.01); *C07K 14/70596* (2013.01); *C07K 16/2896* (2013.01); *C07K 16/30* (2013.01); *C12N 5/0636* (2013.01); *A61K 2039/505* (2013.01); *A61K 2239/17* (2023.05); *A61K 2239/21* (2023.05); *A61K 2239/22* (2023.05); *A61K 2239/29* (2023.05); *A61K 2239/31* (2023.05); *A61K 2239/38* (2023.05); *A61K 2239/48* (2023.05); *C07K 2317/24* (2013.01); *C07K 2317/31* (2013.01); *C07K 2317/53* (2013.01); *C07K 2317/56* (2013.01); *C07K 2317/565* (2013.01); *C07K 2319/02* (2013.01); *C07K 2319/03* (2013.01)

(58) Field of Classification Search
CPC .......... A61K 39/3955; A61K 2039/505; A61K 40/33; A61K 40/00; A61K 40/4212; A61K 39/001113; A61K 39/39558; A61K 40/31; A61K 2239/17; A61K 2239/21; A61K 40/11; C07K 14/70596; C07K 16/2896; C07K 16/2863; C07K 16/30; C07K 2317/24; C07K 2317/53; C07K 2317/56; C07K 2319/02; C07K 2319/03; C12N 5/0636
See application file for complete search history.

(56) References Cited

U.S. PATENT DOCUMENTS

| | | |
|---|---|---|
| 2015/0344573 A1 | 12/2015 | Chang et al. |
| 2017/0340704 A1 | 11/2017 | Pule et al. |
| 2018/0111992 A1 | 4/2018 | Fry et al. |
| 2020/0087396 A1 | 3/2020 | Schneider et al. |

FOREIGN PATENT DOCUMENTS

| | | |
|---|---|---|
| CN | 109836495 A | 6/2019 |
| KR | 10-2020-0003939 A | 1/2020 |
| WO | 98/20734 A1 | 5/1998 |
| WO | 1998-041641 A1 | 9/1998 |
| WO | 1998-042378 A1 | 10/1998 |
| WO | 2017/172981 A2 | 10/2017 |
| WO | 2020-108644 A1 | 6/2020 |

OTHER PUBLICATIONS

Clark et al. CD22: A Regulator of Innate and Adaptive B Cell Responses and Autoimmunity. Front Immunol 9: 2235, 2018 (13 total pages).*
Dorner et al. CD22 and Autoimmune Disease. Int Rev Immunol 31: 363-378, 2012.*
Ereno-Orbea et al. Molecular basis of human CD22 function and therapeutic targeting. Nature Comm 8: 764, 2017 (11 total pages).*
Sullivan-Chang et al. Targeting CD22 in B-cell Malignancies: Current Status and Clinical OutlookBioDrugs 27: 293-3045, 2013.*

(Continued)

*Primary Examiner* — Bridget E Bunner
(74) *Attorney, Agent, or Firm* — ROTHWELL, FIGG, ERNST & MANBECK, P.C.

(57) ABSTRACT

A humanized antibody specific for CD22 and a chimeric antigen receptor using the same, and, in some aspects, a chimeric antigen receptor including the antibody or a CD19xCD22 antibody, a CAR-T cell expressing the chimeric antigen receptor, and a pharmaceutical composition including the same for preventing or treating a disease mediated by B cells.

20 Claims, 19 Drawing Sheets
Specification includes a Sequence Listing.

(56) References Cited

OTHER PUBLICATIONS

Saint Francis Health System, Prevention & Risk Factors, Non-Hodgkin's Lymphoma Prevention, 2023 [accessed Jan. 3, 2024]. Retrieved from the Internet: <https://www.saintfrancis.com/services/cancer-care/cancers-we-treat/non-hodgkins-lymphoma/prevention-and-risk-factors#:~: text=There%20are%20no%20guidelines%20for,maintain%20your%20gluten-free%20diet.>(Year: 2023).

Maude, Shannon L., et al. "Tisagenlecleucel in children and young adults with B-cell lymphoblastic leukemia." New England Journal of Medicine 378.5 (2018): 439-448.

Dai, Hanren et al., 'Bispecific CAR-T cells targeting both CD19 and CD22 for therapy of adults with relapsed or refractory B cell acute lymphoblastic leukemia', Journal of Hematology & Oncology, 2020, vol. 13, article No. 30, pp. 1-10.

Huang, Chen et al., 'Dual specific CD19/CD22-targeted chimeric antigen receptor T-cell therapy for refractory diffuse large B-cell lymphoma: a case report', Oncology Letters, 2020, vol. 20, No. 4, article No. 21, pp. 1-10.

\* cited by examiner

(A) Transfection of CAR gene into HEK293 cell

(B) Binding assay

***huCD22: extracellular domain of CD22 protein (A) CD22-CAR-T culture

***CD22: single chain Fv of humanized anti-CD22 antibody (B) Binding assay

***huCD22 peptide: extracellular domain of CD22 protein

HUMANIZED ANTIBODY SPECIFIC FOR CD22 AND CHIMERIC ANTIGEN RECEPTOR USING THE SAME

CROSS-REFERENCE TO RELATED APPLICATION(S)

This application is a divisional of U.S. patent application Ser. No. 17/563,846 filed on Dec. 28, 2021, which claims priority to and the benefits of Korean Patent Application Nos. KR 10-2020-0187510, filed on Dec. 30, 2020 and KR 10-2021-0070934, filed on Jun. 1, 2021, the entire contents of which are incorporated herein by reference.

The present application includes a Sequence Listing filed in electronic format. The Sequence Listing is entitled "4614-105US2.xml" created on May 17, 2023, and is 76,182 bytes in size. The information in the electronic format of the Sequence Listing is part of the present application and is incorporated herein by reference in its entirety.

TECHNICAL FIELD

The present invention relates to a humanized antibody specific for CD22 and a chimeric antigen receptor using the same, and more specifically, to a humanized antibody specifically binding to CD22, a chimeric antigen receptor including the antibody or a CD19xCD22 antibody, a CAR-T cell expressing the chimeric antigen receptor, and a pharmaceutical composition including the same for preventing or treating a disease mediated by B cells.

BACKGROUND ART

CD22 is expressed in most B cell leukemias and lymphomas, including NHL, acute lymphoblastic leukemia (B-ALL), chronic lymphocytic leukemia (B-CLL) and especially acute non-lymphocytic leukemia (ANLL).

Antibodies specific for CD22 have been developed for the treatment or diagnosis of diseases related to the CD22 expression, and the like. International Publication No. WO1998-041641 discloses a recombinant anti-CD22 antibody having a cysteine residue at the $V_H44$ and $V_L100$ positions, and International Publication No. WO 1998-042378 discloses an anti-CD22 antibody for the treatment of B-cell malignancies.

In order to produce antibodies for treatment as described above, monoclonal antibodies are usually produced using mice. However, non-human antibodies such as mouse-derived monoclonal antibodies are regarded as foreign antigens in the human body and thus have a problem in that the therapeutic effect is limited because they induce an immune response and have a short half-life.

In order to solve the above problems, a humanized antibody has been developed in which the remaining part except for only a region binding to an antigen of an antibody is substituted is a human antibody. As a currently used method for substituting a mouse antibody with a humanized antibody, a human antibody gene most similar to the antibody to be substituted is selected, and only a CDR region of the mouse antibody is substituted with a human antibody CDR position by a method called CDR grafting. The humanized antibody as described above has an advantage in that the immune response in the human body can be reduced because most of the genes are humanized.

Meanwhile, antibodies specific for the various other B cell surface markers (antigens) described above have been developed for the treatment of B cell diseases or disorders, autoimmune diseases, transplantation rejection responses, and the like, and in addition to the CD22 antigen, CD19 is an antigen that is commonly used as a target, and clinical studies on CAR-T cells targeting CD19 are also significantly progressing. However, there is a difference in the expression level of the target antigen depending on the cells such as leukemia that does not express CD19, and for a single CAR or single CAR-T cell therapy targeting only one antigen, a problem such as loss of the target antigen may occur due to the immune evasion strategy of tumor cells. In fact, in the case of patients with B cell acute lymphoblastic leukemia (ALL), CD19-negative recurrence in which CD19 was not expressed was observed (up to 25% of patients with B-cell ALL, who responded to CD19 CAR-T therapy for the first time), and this phenomenon was found to be a mechanism of tumor cell resistance to the CAR-T cell treatment (Maude, S. L., et al., *N. Engl. I. Med.*, 378:439-448, 2018).

To solve this problem, CAR-T cells targeting double or multiple antigens have been studied, and targeting two antigens at the same time can reduce the possibility of antigen-loss variants.

DISCLOSURE

Technical Problem

In the present invention, a humanized anti-CD22 antibody was prepared by selecting an antibody binding to CD22 and using the antibody binding to CD22 in order to reduce an immune response in the human body, and using the humanized anti-CD22 antibody of the present invention, a chimeric antigen receptor and CAR-T cells were prepared.

Furthermore, a bispecific chimeric antigen receptor (bivalent CAR or bispecific CAR) targeting not only CD22 but also CD19 and bispecific CAR-T cells were prepared, and it was confirmed that the chimeric antigen receptor was normally expressed in the CD22-CAR-T cells and bispecific CD19xCD22-CAR-T cells prepared in the present invention, thereby completing the present invention.

An object of the present invention is to provide a humanized antibody specific for CD22, a polynucleotide encoding the antibody, a vector expressing the antibody, and a recombinant cell transformed with the vector.

Another object of the present invention is to provide a chimeric antigen receptor including the humanized antibody specific for CD22, a polynucleotide encoding the chimeric antigen receptor, a vector including the polynucleotide, and an immune effector cell expressing a chimeric antigen receptor, which includes the polynucleotide or vector.

Still another object of the present invention is to provide a bispecific chimeric antigen receptor including an antibody specific for CD19 and CD22, a polynucleotide encoding the bispecific chimeric antigen receptor, a vector including the polynucleotide, and an immune effector cell expressing a bispecific chimeric antigen receptor, and an immune effector cell expressing a bispecific chimeric antigen receptor, which includes the polynucleotide or vector.

Yet another object of the present invention is to provide a pharmaceutical composition including the immune effector cell for preventing or treating a disease mediated by B cells.

Technical Solution

To achieve an object among the above-described objects, the present invention provides a humanized antibody specifically binding to CD22 or a fragment thereof, including: a heavy chain variable region represented by an amino acid sequence of SEQ ID NO: 11 and a light chain variable region represented by an amino acid sequence of SEQ ID NO: 12; or a heavy chain variable region represented by an amino acid sequence of SEQ ID NO: 15 and a light chain variable region represented by an amino acid sequence of SEQ ID NO: 16.

Further, the present invention provides a polynucleotide encoding the humanized antibody specifically binding to CD22 or the fragment thereof.

In addition, the present invention provides a vector including a polynucleotide encoding the humanized antibody specifically binding to CD22 or the fragment thereof.

Furthermore, the present invention provides a recombinant cell producing the humanized antibody specifically binding to CD22 transformed with the vector, or the fragment thereof.

To achieve another object, the present invention provides a chimeric antigen receptor (CAR) targeting CD22, including: a CD22-binding domain; a transmembrane domain; a costimulatory domain; and an intracellular signal transduction domain, in which the CD22-binding domain is a humanized antibody specifically binding to CD22 or a fragment thereof, including a heavy chain variable region represented by an amino acid sequence of SEQ ID NO: 11 and a light chain variable region represented by an amino acid sequence of SEQ ID NO: 12; or a heavy chain variable region represented by an amino acid sequence of SEQ ID NO: 15 and a light chain variable region represented by an amino acid sequence of SEQ ID NO: 16.

In a preferred exemplary embodiment of the present invention, the transmembrane domain may be a protein selected from the group consisting of CD8α, CD4, CD28, CD137, CD80, CD86, CD152 and PD1, the costimulatory domain may be a protein selected from the group consisting of CD28, 4-1BB, OX-40 and ICOS, and the intracellular signal transduction domain may be derived from CD3ζ.

In another preferred exemplary embodiment of the present invention, a hinge region located between the C-terminus of the CD22-binding domain and the N-terminus of a transmembrane domain may be further included, and the hinge region may be derived from CD8α.

Further, the present invention provides a polynucleotide encoding the chimeric antigen receptor.

In addition, the present invention provides a vector including a polynucleotide encoding the chimeric antigen receptor.

Furthermore, the present invention provides an immune effector cell including a polynucleotide encoding the chimeric antigen receptor or a vector including the polynucleotide, and expressing the chimeric antigen receptor.

To achieve another object, the present invention provides a bispecific chimeric antigen receptor (CAR) targeting CD19 and CD22, including: a CD19-binding domain and a CD22-binding domain;

a transmembrane domain;

a costimulatory domain; and an intracellular signal transduction domain, in which the CD22-binding domain is an antibody specifically binding to CD22 or a fragment thereof, including a heavy chain variable region including a CDR1 region represented by an amino acid of SEQ ID: 1, a CDR2 region represented by an amino acid of SEQ ID NO: 2 and a CDR3 region represented by an amino acid of SEQ ID NO: 3 and a light chain variable region including a CDR1 region represented by an amino acid of SEQ ID NO: 4, a CDR2 region represented by an amino acid of SEQ ID NO: 5 and a CDR3 region represented by an amino acid of SEQ ID NO: 6.

In a preferred exemplary embodiment of the present invention, the CD19-binding domain and the CD22-binding domain may be linked in the order of a light chain variable region of an antibody specifically binding to CD19—a heavy chain variable region of an antibody specifically binding to CD22—a light chain variable region of an antibody specifically binding to CD22—a heavy chain variable region of an antibody specifically binding to CD19.

In another preferred exemplary embodiment of the present invention, the light chain variable region of the antibody specifically binding to CD19 may include a CDR1 region represented by an amino acid of SEQ ID NO: 44, a CDR2 region represented by an amino acid of SEQ ID NO: 45 and a CDR3 region represented by an amino acid of SEQ ID NO: 46, and may be preferably represented by an amino acid sequence of SEQ ID NO: 48.

In still another exemplary embodiment of the present invention, the heavy chain variable region of the antibody specifically binding to CD19 may include a CDR1 region represented by an amino acid of SEQ ID NO: 41, a CDR2 region represented by SEQ ID NO: 42 and a CDR3 region represented by an amino acid of SEQ ID NO: 43, and may be preferably represented by an amino acid sequence of SEQ ID NO: 47.

In yet another preferred exemplary embodiment of the present invention, the transmembrane domain may be a protein selected from the group consisting of CD8α, CD4, CD28, CD137, CD80, CD86, CD152 and PD1, the costimulatory domain may be a protein selected from the group consisting of CD28, 4-1BB, OX-40 and ICOS, and the intracellular signal transduction domain may be derived from CD3ζ.

In yet another preferred exemplary embodiment of the present invention, a hinge region located between the C-terminus of the CD22-binding domain and the N-terminus of a transmembrane domain may be further included, and the hinge region may be derived from CD8α.

Further, the present invention provides a polynucleotide encoding the bispecific chimeric antigen receptor.

In addition, the present invention provides a vector including a polynucleotide encoding the bispecific chimeric antigen receptor.

Furthermore, the present invention provides an immune effector cell including a polynucleotide encoding the bispecific chimeric antigen receptor or a vector including the polynucleotide, and expressing the bispecific chimeric antigen receptor.

To achieve another object, the present invention provides a pharmaceutical composition including: the humanized antibody specifically binding to CD22 or the fragment thereof; or the immune effector cell for preventing or treating a disease mediated by B cells.

In a preferred exemplary embodiment of the present invention, the disease mediated by B cells may be selected from the group consisting of tumors, lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma (SLL), leukemia, hairy cell leukemia (HCL), acute lymphocytic leukemia (ALL), Burkitt's lymphoma and mantle cell lymphoma.

Advantageous Effects

In the present invention, a humanized antibody specifically binding to CD22 was prepared, and single CAR-T cells targeting CD22 and bispecific CAR-T cells targeting CD19 and CD22 were prepared using the same.

It was confirmed that the CD22-CAR-T cells and bispecific CD19xCD22-CAR-T cells prepared in the present invention effectively recognized a CD22 antigen to activate CAR-T cells, and that the CD22-CAR-T cells and bispecific CD19xCD22-CAR-T cells effectively killed cells expressing CD22.

Furthermore, since it was confirmed that the bispecific CD19xCD22-CAR-T cells exhibited excellent antitumor effects in an animal model, the humanized antibody-based CD22-CAR-T cells and bispecific CD19xCD22-CAR-T cells specifically binding to CD22 of the present invention can be usefully utilized as a composition for preventing or treating a disease related to the expression of CD22 (or CD19) or a disease related to B cells.

MODES OF THE INVENTION

Figure 1:
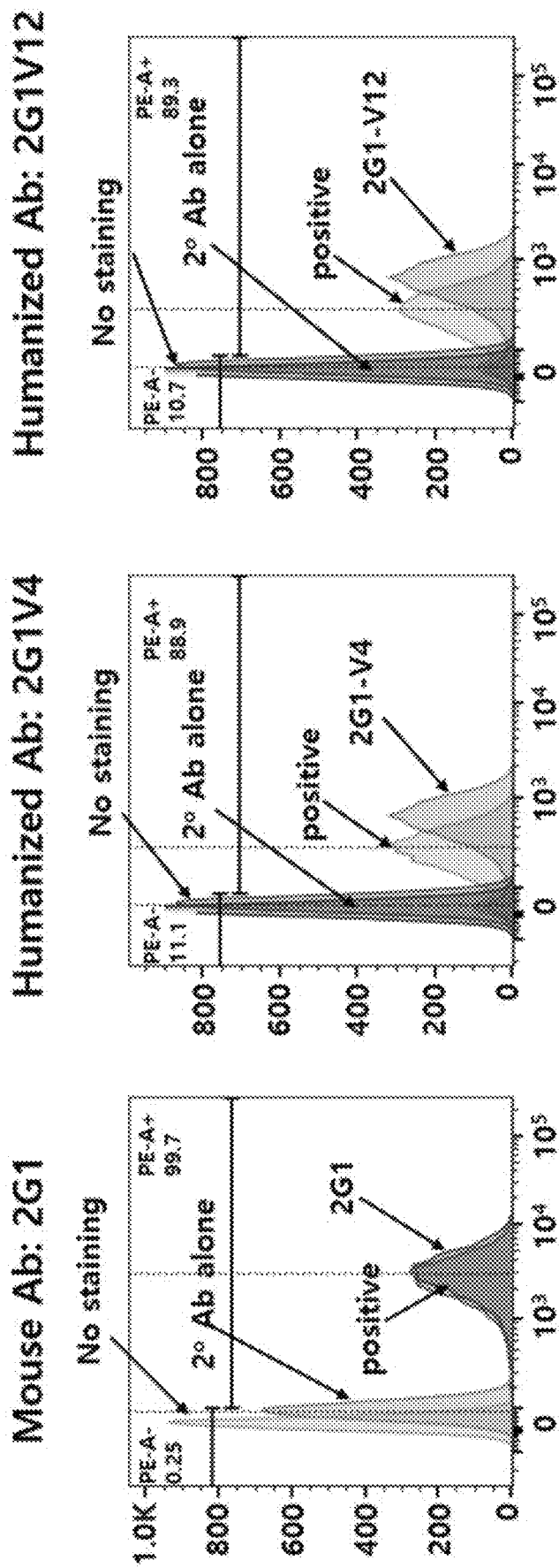
FIG. 1 illustrates the data confirming the binding force of the 2G1 antibody and the humanized 2G1 antibody selected in the present invention to CD22 by FACS.
Figure 2:
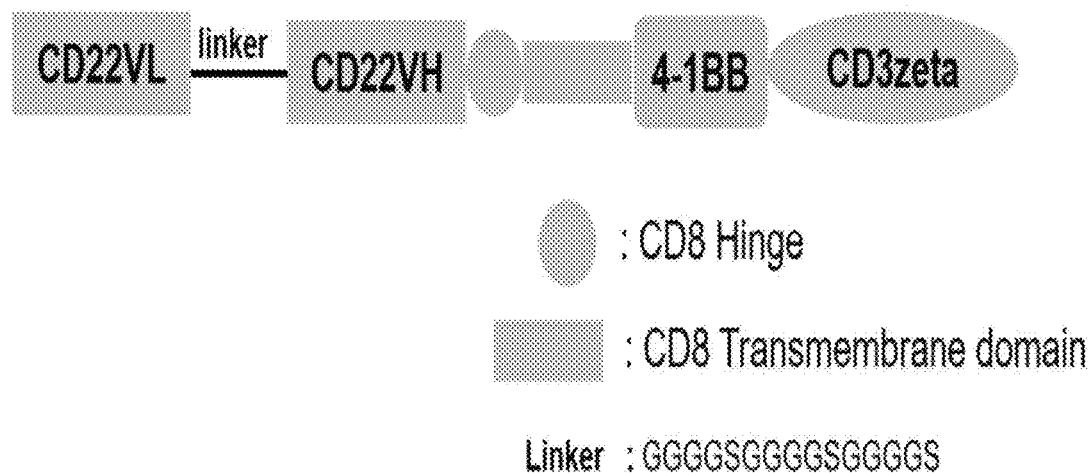
FIG. 2 is a schematic view illustrating a chimeric antigen receptor (single CAR) targeting CD22. Linker is the amino acid sequence of SEQ ID NO: 19.

Hereinafter, the present invention will be described in detail.
Humanized Antibody Specifically Binding to CD22

In an aspect, the present invention relates to a humanized antibody specifically binding to CD22 or a fragment thereof, including: a heavy chain variable region represented by an amino acid sequence of SEQ ID NO: 11 and a light chain variable region represented by an amino acid sequence of SEQ ID NO: 12; or
 a heavy chain variable region represented by an amino acid sequence of SEQ ID NO: 15 and a light chain variable region represented by an amino acid sequence of SEQ ID NO: 16.

As used herein, the term "humanized antibody" refers to an antibody made using one of the techniques for possessing an amino acid sequence corresponding to an antibody produced by a human and/or making the human antibody as disclosed herein. Such a definition of the humanized antibody specifically excludes a humanized antibody including a non-human antigen binding residue.

In the present invention, the antibody may be a monoclonal antibody. As used herein, the term "monoclonal antibody" is also called a single clonal antibody, and is an antibody which is produced by single antibody-forming cells and is characterized as having a uniform primary structure (amino acid arrangement). The monoclonal antibody recognizes only one antigenic determinant and is generally produced by culturing a hybridoma cell, which is a fusion of cancer cells and antibody-producing cells, but may also be produced using other recombinant protein-expressing host cells using a secured antibody genetic sequence. In addition, the antibody may also be used by humanizing the remaining portion excluding the CDR portion, if necessary.

As used herein, the term "CDR", that is, "complementarity determining region" refers to a non-contiguous antigen-binding site found in the variable regions of both heavy chain and light chain regions As used herein, the term "antibody" may be used not only in a full form with two full-length light chains and two full-length heavy chains, but also in the form of a fragment of an antibody molecule. The fragment of an antibody molecule refers to a fragment at least having a peptide tag (epitope) binding function, and includes scFv, Fab, F(ab'), F(ab'), a single domain and the like.

Among the antibody fragments, Fab has one antigen-binding site with a structure having variable regions of a light chain and a heavy chain and a constant region of the light chain and a first constant region (CH1) of the heavy chain. Fab' differs from Fab in that Fab∝ has a hinge region including one or more cysteine residues at the C-terminus of the heavy chain CH1 domain. The F(ab')2 antibody is produced while the cysteine residue of the hinge region of Fab' forms a disulfide bond. Fv is a minimal antibody fragment having only a heavy chain variable region and a light chain variable region, a double chain Fv(dsFv) has a heavy chain variable region linked with a light chain variable region by a disulfide bond, and a single chain Fv(scFv) has a heavy chain variable region linked with a light chain variable region by a covalent bond generally through a peptide linker. Such an antibody fragment may be obtained using a proteolytic enzyme or preferably constructed by a gene recombination technique.

The monoclonal antibody specifically binding to CD22 of the present invention may be prepared using all or part of the CD22 protein as an immunogen (or an antigen). More specifically, first, immunization is achieved by subcutaneous, intramuscular, intravenous, intra-footpad or intraperitoneal injection of a CD22 protein, a fusion protein including the CD22 protein, or a carrier containing the CD22 protein as an immunogen into a mammal other than a human once to several times, together with an immune enhancer adjuvant (for example, a Freund's adjuvant) if necessary. The mammal other than the human is preferably a mouse, a rat, a hamster, a guinea pig, a chicken, a rabbit, a cat, a dog, a pig, a goat, a sheep, a donkey, a horse or a cow (including a transgenic animal manipulated to produce an antibody derived from other animals such as a transgenic mouse producing a human antibody), and more preferably a mouse, a rat, a hamster, a guinea pig, a chicken, or a rabbit. By performing immunization 1 to 4 times every 1 to 21 days from the initial immunization, antibody-producing cells can be obtained from the immune-sensitized mammal approximately 1 to 10 days after the final immunization. The number of immunizations and the time interval can be appropriately changed according to the characteristics and the like of the immunogen used.

Hybridomas secreting the monoclonal antibody can be prepared according to the method of Kohler and Milstein, et al. (Nature, 1975, Vol. 256, p.495-49'7) or a method equivalent thereto. The hybridomas can be prepared by the cell fusion of antibody-producing cells included in any one selected from the group consisting of the spleen, lymph nodes, bone marrow or the tonsils, preferably the spleen, obtained from the animal other than a human, which is immune-sensitized as described above, with myeloma cells derived from a mammal lacking the ability to produce autoantibodies. The mammal may be a mouse, a rat, a guinea pig, a hamster, a chicken, a rabbit or a human, and may be preferably a mouse, a rat, a chicken, or a human.

For cell fusion, for example, a fusion accelerator such as polyethylene glycol or Sendai virus or a method using an electric pulse is used, and as an example, antibody-producing cells and mammal-derived cells capable of infinite proliferation are suspended in a fusion medium containing a fusion promoter at a ratio of about 1:1 to 1:10, and in this state, cultured at about 30 to 40° C. for about 1 to 5 minutes. As the fusion medium, for example, typical general media such as MEM medium, RPMI1640 medium, and Iscove's Modified Dulbecco's Medium may be used, and serum such as bovine serum is preferably excluded.

For a method for screening a hybridoma clone producing the monoclonal antibody, first, the fusion cells obtained as described above are transferred to a selection medium such as a HAT medium, and cultured at about 30 to 40° C. for about 3 days to 3 weeks to kill cells other than the hybridoma. Subsequently, the method may be performed by a method of culturing the hybridoma in a microtiter plate, and the like, and then searching for a portion where the reactivity between the immunogen used for an immune response of the animal other than the human as described above and a culture supernatant is increased by an immunoassay such as radioactive substance-marked immuno antibody (RIA) or Enzyme-Linked Immunosorbent Assay (ELISA). Also, a clone producing the monoclonal antibody found above shows a specific binding force to the immunogen.

The monoclonal antibody of the present invention may be obtained by culturing such a hybridoma in vitro or in vivo. For culturing, a typical method for culturing mammal-derived cells is used, and to collect a monoclonal antibody from a culture or the like, a typical method in this field for purifying antibodies in general is used. Examples of each method include salting out, dialysis, filtration, concentration, centrifugation, separatory sedimentation, ion-exchange chromatography, gel filtration chromatography, ion-exchange chromatography, affinity chromatography, high-performance liquid chromatography, gel electrophoresis, isoelectric point electrophoresis, and the like, and these are applied in combination, if necessary. The purified monoclonal antibody is then concentrated and dried to be made into a liquid or solid form depending on the application.

Further, the monoclonal antibody of the present invention may be obtained by synthesizing a gene which links DNA encoding variable regions of a heavy chain and a light chain to already-known DNA encoding each of the constant regions of the heavy chain and the light chain (for example, see Japanese Patent No. 2007-252372) by a PCR method or chemical synthesis, transplanting the gene into a known expression vector (pcDNA 3.1 (sold by Invitrogen)) that enables the expression of the gene, and the like to prepare a transformant, expressing the gene in a host such as CHO cells or *E. coli* to produce an antibody, and using Protein A or G columns and the like to purify the antibody from the culture solution.

In a specific exemplary embodiment of the present invention, in order to prepare an antibody specifically binding to CD22, an antibody (scFv) specifically binding to CD22 was selected by preparing and screening a hybridoma which produces an anti-CD22 antibody, and was named 2G1.

It was confirmed that the 2G1 antibody included a heavy chain variable region including a CDR1 region (GFSLT-SYDI) represented by an amino acid of SEQ ID NO: 1, a CDR2 region (IWTGGGT) represented by an amino acid of SEQ ID NO: 2 and a CDR3 region (VPHYYGYAMDYW) represented by an amino acid of SEQ ID NO: 3 and a light chain variable region including a CDR1 region (QDINKY) represented by an amino acid of SEQ ID NO: 4, a CDR2 region (YTS) represented by an amino acid of SEQ ID NO: 5 and a CDR3 region (LQYDNLLT) represented by an amino acid of SEQ ID NO: 6.

Specifically, it was confirmed that the 2G1 antibody included a heavy chain variable region represented by an amino acid of SEQ ID NO: 7 and a light chain variable region represented by an amino acid of SEQ ID NO: 8, the heavy chain variable region was encoded by a base sequence of SEQ ID NO: 9, and the light chain variable region was encoded by a base sequence of SEQ ID NO: 10.

In another specific exemplary embodiment of the present invention, a humanized antibody in which the anti-CD22 antibody 2G1 was modified to a structure corresponding to a human was prepared, and named 2G1(V4) and 2G1(V12).

The heavy chain variable region CDR and light chain variable region CDR of the 2G1(V4) and 2G1(V12) were similar to 2G1, and the remaining portion except for the CDR portion was humanized. Preferably, 2G1(V4) includes a heavy chain variable region represented by an amino acid of SEQ ID: 11 and a light chain variable region represented by SEQ ID NO: 12, and the heavy chain variable region and light chain variable region of the 2G1(V4) antibody may be encoded by a base sequence of SEQ ID NO: 13 and a base sequence of SEQ ID NO: 14, respectively.

In addition, 2G1(V12) includes a heavy chain variable region represented by an amino acid sequence of SEQ ID NO: 15 and a light chain variable region represented by an amino acid sequence of SEQ ID NO: 16, and the heavy chain variable region and light chain variable region of the 2G1 (V12) antibody may be encoded by a base sequence of SEQ ID NO: 17 and a base sequence of SEQ ID NO: 18, respectively.

The antibody specific for CD22 of the present invention is a single chain variable fragment (scFv), and may be constructed by a gene recombination technique such that the heavy chain variable region and the light chain variable region can be linked by a linker. The linker may be preferably represented by an amino acid sequence of SEQ ID NO: 19, or encoded by a base sequence of SEQ ID NO: 20, SEQ ID NO: 21, or SEQ ID NO: 22, but is not limited thereto.

When being linked as light chain variable region-linker-light chain variable region, the 2G1 antibody (mouse antibody) may be represented by an amino acid sequence of SEQ ID NO: 23, or encoded by a base sequence of SEQ ID NO: 24, the 2G1(V4) antibody may be represented by an amino acid sequence of SEQ ID NO: 25 or encoded by a base sequence of SEQ ID NO: 26, and the 2G1(V12) antibody may be represented by an amino acid sequence of SEQ ID NO: 27 or encoded by a base sequence of Seq ID NO: 28.

In another aspect, the present invention relates to a polynucleotide encoding the antibody specifically binding to CD22.

As used herein, the term "oligonucleotide" generally refers to a nucleic acid molecule, a deoxyribonucleotide or a ribonucleotide, or an analog thereof, separated by an arbitrary length. The polynucleotide may be prepared by (1) in-vitro amplification, such as polymerase chain reaction (PCR) amplification; (2) cloning and recombination; (3) purification such as digestion and gel electrophoresis separation; or (4) synthesis, such as chemical synthesis, and preferably, the separated polynucleotide may be prepared by a recombinant DNA technique. In the present invention, a polynucleotide for encoding an antibody or an antigen-binding fragment thereof may be prepared by various methods known in the art, including, but not limited to, the restriction fragment operation of synthetic oligonucleotides or the application of SOE PCR.

In still another aspect, the present invention relates to a vector including the polynucleotide encoding the antibody specifically binding to CD22, and a recombinant cell transformed with the vector.

As used herein, the term "expression vector" refers to a gene product including an essential regulatory element such as a promoter such that a target gene can be expressed in a suitable host cell. The vector may be selected from one or more of a plasmid, a retroviral vector and a lentiviral vector. Once transformed into a suitable host, the vector may be replicated and function independently of the host genome, or may be integrated into the genome itself in some cases.

Furthermore, the vector may include an expression control element that allows a coding region to be accurately expressed in a suitable host. Such a regulatory element is well known to those skilled in the art, and may include, for example, a promoter, a ribosome-binding site, an enhancer and other regulatory elements to regulate gene transcription or mRNA translation. A specific structure of an expression regulatory sequence may vary depending on the function of the species or cell type, but generally contains a 5' non-transcriptional sequence and a 5' or 3' non-translational sequence that participate in transcription initiation and translation initiation, such as a TATA box, a capped cupping sequence, and a CAAT sequence, respectively. For example, a 5' non-transcription expression regulatory sequence may include a promoter region capable of including a promoter sequence for transcribing and regulating functionally linked nucleic acids.

As used herein, the term "promoter" refers to a minimal sequence sufficient to direct transcription. Further, a promoter configuration sufficient to express a regulatory promoter-dependent gene induced by a cell type-specific or external signal or agent may be included, and the configurations may be located at the 5' or 3' portion of the gene. Both a conservative promoter and an inducible promoter are included. The promoter sequence may be derived from a prokaryote, eukaryote, or virus.

As used herein, the term "transformant" refers to a cell transformed by introducing a vector having a polynucleotide encoding one or more target proteins into a host cell, and examples of a method for preparing a transformant by introducing an expression vector into a host cell include a calcium phosphate method or calcium chloride/rubidium chloride method, electroporation, electroinjection, a chemical treatment method such as PEG, a method using a gene gun and the like, and the like described in the literature (Sambrook, J., et al., Molecular Cloning, A Laboratory Manual (2nd edition), Cold Spring Harbor Laboratory, 1.74, 1989).

A large amount of antibody protein can be prepared and separated by culturing a transformant in which the vector is expressed in a nutrient medium. Medium and culture conditions may be appropriately selected and used depending on the host cell. During culturing, conditions such as temperature, pH of the medium and duration of the culture should be adjusted appropriately so as to be suitable for growth of cells and mass production of proteins.

The vector according to the present invention may be transformed into a host cell, preferably a mammalian cell, for the production of antibodies. A number of suitable host cell lines capable of expressing a fully glycosylated protein have been developed in the art, and include COS-1 (for example, ATCC CRL 1650), COS-7 (for example, ATCC CRL-1651), HEK293, BHK21 (for example, ATCC CRL-10), CHO (for example, ATCC CRL 1610) and BSC-1(for example, ATCC CRL-26) cell lines, Cos-7 cells, CHO cells, hep G2 cells, P3X63Ag8653, SP2/0-Ag14, 293 cells, HeLa cells, and the like, and these cells are readily available, for example, from the ATCC (American Type Collection, USA). Preferred host cells include cells originating from lymphocytes such as melanoma and lymphoma cells.

Chimeric Antigen Receptor Targeting CD22

In yet another aspect, the present invention relates to a chimeric antigen receptor (CAR) targeting CD22, including:
a CD22-binding domain;
a transmembrane domain;
a costimulatory domain; and
an intracellular signal transduction domain,
in which the CD22-binding domain is a humanized antibody specifically binding to CD22 or a fragment thereof, including a heavy chain variable region represented by an amino acid sequence of SEQ ID NO: 11 and a light chain variable region represented by an amino acid sequence of SEQ ID NO: 12; or
a heavy chain variable region represented by an amino acid sequence of SEQ ID NO: 15 and a light chain variable region represented by an amino acid sequence of SEQ ID NO: 16.

As used herein, the term "chimeric antigen receptor (CAR)" generally refers to a fusion protein containing an antigen and an extracellular domain having the ability to bind to one or more intracellular domains. CAR is a core part of the chimeric antigen receptor T cell (CAR-T), and may include an antigen binding domain, a transmembrane domain, costimulatory domain and an intracellular signal transduction domain. CAR may be combined with a T cell receptor-activated intracellular domain based on the antigen (for example, CD22) specificity of the antibody. CAR-expressing T cells with a modified gene may specifically identify and eliminate target antigen-expressing malignant cells.

As used herein, the term "CD22-binding domain" generally refers to a domain capable of specifically binding to a CD22 protein. For example, the CD22-binding domain may contain an anti-CD22 antibody or fragment thereof capable of specifically binding to a human CD22 polypeptide expressed in B cells or a fragment thereof.

As used herein, the term "binding domain" may be used interchangeably with "extracellular domain", "extracellular binding domain", "antigen-specific binding domain" and "extracellular antigen-specific binding domain", and refers to a CAR domain or a fragment thereof which has the ability to specifically bind to a target antigen (for example, CD22).

In the present invention, the anti-CD22 antibody or the fragment thereof is a monoclonal antibody, preferably a single chain variable fragment (scFv) as the above-described anti-CD22 antibody. Specifically, the anti-CD22 antibody or the fragment thereof may be prepared using a 2G1(V4) or 2G1(V12) antibody, which is the humanized antibody specific to CD22 of the present invention.

In the present invention, the chimeric antigen receptor may be a bispecific chimeric antigen receptor further including a B cell surface marker-binding domain in addition to the CD22-binding domain, and the B cell surface marker may be CD1O, CD19, CD20, CD21, CD22, CD23, CD24, CD37, CD53, CD72, CD74, CD75, CD77, CD79a, CD79b, CD80, CD81, CD82, CD83, CD84, CD85 or CD86, and may be preferably CD19.

In the present invention, a signal peptide may be further included at the N-terminus of the CD22-binding domain, and the "signal peptide" generally refers to a peptide chain for guiding protein transduction. The signal peptide may be a short peptide having a length of 5 to 30 amino acids, and an amino acid sequence of SEQ ID NO: 36 was preferably used in the present invention.

In the present invention, a hinge region located between the C-terminus of the CD22-binding domain and the N-terminus of the transmembrane domain may be further included, and the hinge region is derived from CD8α and may be represented by an amino acid sequence of SEQ ID NO: 37. The "hinge region" generally refers to a linking region between an antigen-binding site and an immune cell Fc receptor (FcR)-binding region.

As used herein, the "transmembrane domain" generally refers to a domain of CAR that passes through a cell membrane and is linked to an intracellular signal transduction domain to play a role in signal transduction. The transmembrane domain may be derived from a protein selected from the group consisting of CD8α, CD4, CD28, CD137, CD80, CD86, CD152 and PD1, and may be preferably represented by an amino acid sequence of SEQ ID NO: 38.

As used herein, the "costimulatory domain" generally refers to an intracellular domain capable of providing an immunostimulatory molecule which is a cell surface molecule required for an effective response of lymphocytes to an antigen. The above-described costimulatory domain may include a costimulatory domain of CD28, may include a costimulatory domain of a TNF receptor family, such as a costimulatory domain of OX40 and 4-1BB, and may be preferably 4-1BB represented by an amino acid sequence of SEQ ID NO: 39.

As used herein, the "intracellular signal transduction domain" generally refers to a domain located inside a cell and capable of transducing a signal. In the present invention, the intracellular signal transduction domain is an intracellular signal transduction domain of a chimeric antigen receptor. For example, the intracellular signal transduction domain may be selected from an intracellular domain of CD3ζ, an intracellular domain of CD28, an intracellular domain of CD28, an intracellular domain of 4-1BB and an intracellular domain of OX40, and may be preferably CD3represented by an amino acid sequence of SEQ ID NO: 40.

Polynucleotide Encoding Chimeric Antigen Receptor and Chimeric Antigen Receptor Expression Vector In yet another aspect, the present invention relates to a polynucleotide encoding the chimeric antigen receptor (CAR).

In the present invention, a polynucleotide encoding the chimeric antigen receptor (CAR) may include: a polynucleotide encoding a CD22-binding domain; a polynucleotide encoding a transmembrane domain; a polynucleotide encoding a costimulatory domain; and a polynucleotide encoding an intracellular signal transduction domain.

The polynucleotide encoding the CD22-binding domain may be a humanized 2G1(V4) or 2G1(V12) antibody specific for CD22 of the present invention, is in the form of a scFv in which a light chain variable region and a heavy chain variable region are linked by a linker, and a specific base sequence thereof is as described above.

Preferably, the polynucleotide encoding the chimeric antigen receptor (CAR) of the present invention may include: a 2G1(V4) antibody represented by a base sequence of SEQ ID NO: 26 or a 2G1(V12) antibody represented by a base sequence of SEQ ID NO: 28;
 a transmembrane domain represented by a base sequence of SEQ ID NO: 32;
 4-1BB (costimulatory domain) represented by a base sequence of SEQ ID NO: 33; and
 CD3ζ (intracellular signal transduction domain) represented by a base sequence of SEQ ID NO: 34.

When a signal peptide is included at the N-terminus of the CD22-binding domain, a signal peptide represented by a base sequence of SEQ ID NO: 30 may further included. Further, a polynucleotide encoding a hinge region may be further included between the polynucleotide encoding the CD22-binding domain and the transmembrane domain, and may be preferably a CD8 hinge region represented by a base sequence of SEQ ID NO: 31.

In yet another aspect, the present invention relates to a vector including the polynucleotide encoding the chimeric antigen receptor (CAR).

Figure 3:
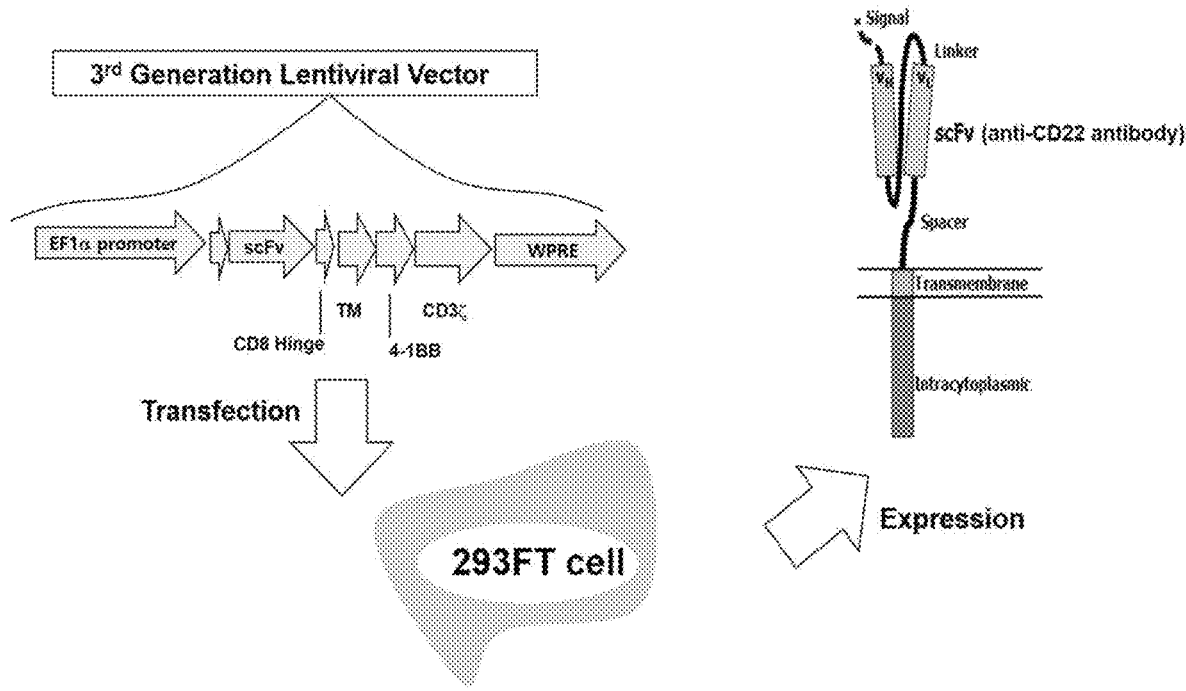
FIG. 3 is a schematic view illustrating a method for preparing CD22-CAR-expressing cells using a lentivirus expressing CD22-CAR.

In the present invention, the vector is a recombinant viral vector, preferably, a lentiviral vector, and includes: an operably linked EF1a promoter; a polynucleotide encoding a signal peptide; a polynucleotide encoding a CD22-binding domain; a polynucleotide encoding a transmembrane domain; and a polynucleotide encoding an intracellular signal transduction domain, and may further include a woodchuck hepatitis virus post-transcriptional regulatory element (WPRE) in order to increase protein expression (FIG. 3).

The EF1α promoter may be represented by a base sequence of SEQ ID NO: 29, and may include a sequence which is 90% or more, 93% or more, 95% or more, 96% or more, 97% or more, 98% or more, or 99% or more identical to the base sequence of SEQ ID NO: 27, if necessary.

In addition, the promoter is operably linked to induce the expression of an anti-CD22 antibody (scFv), which is a CD22-binding domain.

Figure 5:
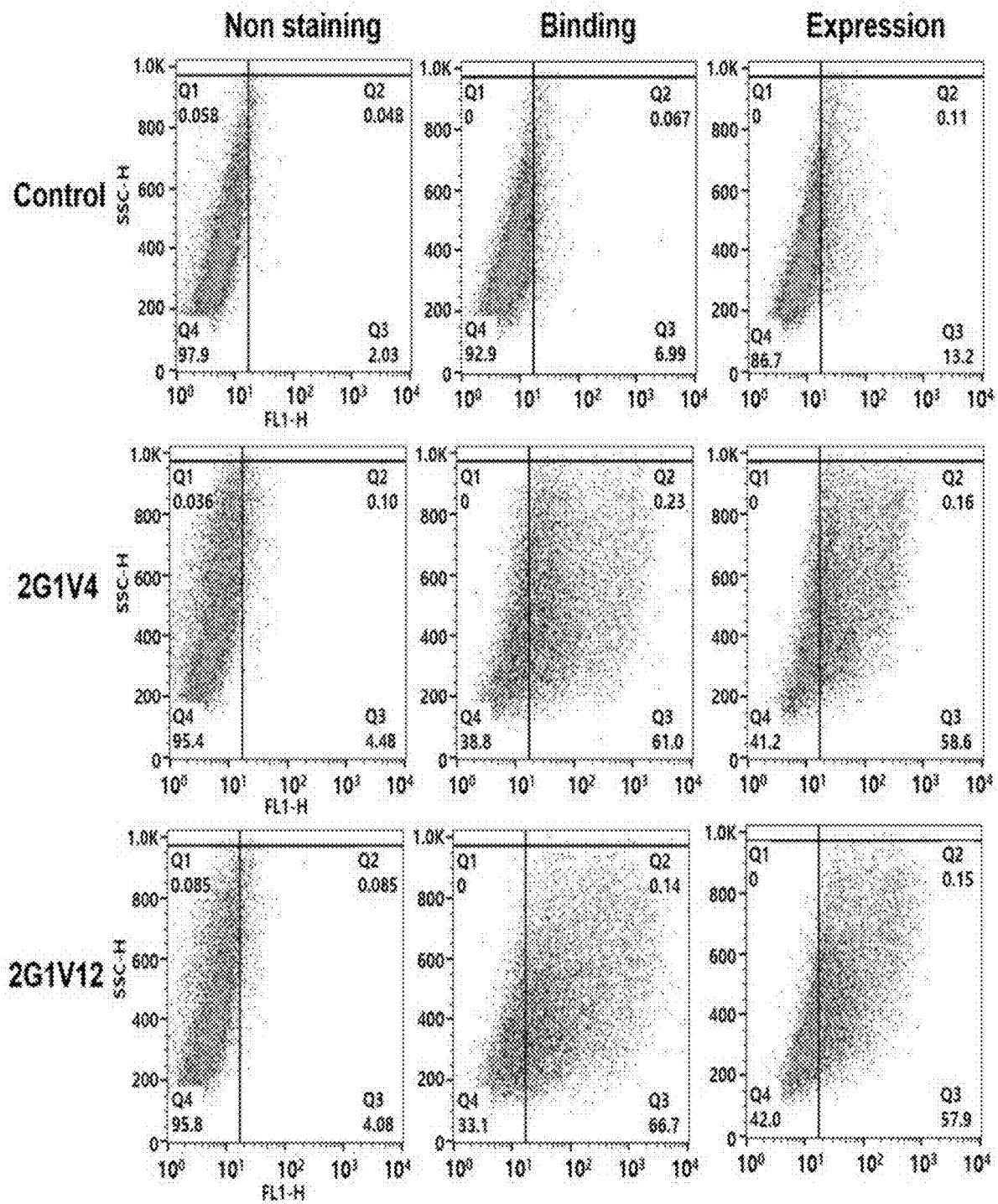
FIG. 5 illustrates the data confirming the expression level of CD22-CAR in HEK293FT cells transformed with the lentivirus expressing 2G1(V4) and 2G1(V12)-based CD22-CAR, which are humanized anti-CD22 antibodies.

In a specific exemplary embodiment of the present invention, as illustrated in FIG. 3, a lentiviral vector into which a polynucleotide encoding CD22-CAR was inserted was prepared, and CD22-CAR expressing cells were prepared by transforming 293FT cells with the prepared vector. Furthermore, as illustrated in FIG. 5, it was confirmed that a chimeric antigen receptor targeting CD22 was expressed in the prepared CD22-CAR expressing cells.

A biological method for introducing a polynucleotide into a host cell includes the use of DNA and RNA vectors. Viral vectors and particularly retroviral vectors have become the most widely used methods for inserting genes into mammals, for example, human cells. Other viral vectors may be derived from lentiviruses, poxviruses, herpes simplex viruses, adenoviruses and adeno-related viruses, and the like.

A chemical means for introducing a polynucleotide into a host cell includes a colloidal dispersion system, such as a macromolecular complex, a nanocapsule, a microsphere, a bead, and a lipid-based system including an oil-in-water emulsion, a micelle, a mixed micelle, and a liposome. An exemplary colloidal system for use as a delivery vehicle in vitro and in vivo is a liposome (for example, an artificial membrane vesicle). Another method is available for a state-of-the-art delivery of nucleic acids, for example, a delivery of a polynucleotide using targeted nanoparticles or another suitable sub-micron-sized delivery system.

When a non-viral delivery system is used, an exemplary delivery vehicle is a liposome. The use of a lipid preparation is considered for the introduction of a nucleic acid into a host cell (in vitro, ex vivo or in vivo). In another aspect, the nucleic acid may be associated with a lipid. The nucleic acid associated with the lipid may be encapsulated in an aqueous solution of liposomes, interspersed in a bilayer of liposomes, attached to liposomes through a linking molecule associated with both liposomes and oligonucleotides, or captured in liposomes, or complexed with liposomes, or dispersed in a lipid-containing solution, or mixed with the lipid, or combined with the lipid, or contained in the lipid as a suspension, or contained or complexed with a micelle, or associated unlike the lipid. The lipid, lipid/DNA or lipid/expression vector association composition is not limited to any specific structure in a solution.

Immune Effector Cell Expressing Chimeric Antigen Receptor (CAR)

In yet another aspect, the present invention relates to an immune effector cell, which includes a vector including a polynucleotide encoding the humanized antibody-based chimeric antigen receptor (CAR) specific for CD22 or a polynucleotide encoding the chimeric antigen receptor (CAR), and expresses the humanized antibody-based chimeric antigen receptor (CAR) specific for CD22.

In the present invention, the immune effector cell may be an isolated cell derived from mammals, preferably a T cell, a B cell, a natural killer (NK) cell, a dendritic cell, a bone marrow cell, a mononuclear cell or a macrophage, and more preferably a T cell.

In the present invention, the immune effector cell expressing the chimeric antigen receptor (CAR) may be prepared by introducing the CAR vector of the present invention into an immune effector cell, for example, a T cell or an NK cell.

Specifically, the CAR vector may be introduced into cells by methods known in the art, such as electroporation and Lipofectamine 2000 (Invitrogen). For example, the immune effector cell may be transfected with a lentiviral vector to integrate a viral genome carrying the CAR molecule into a host genome, ensuring long-term and stable expression of the target gene. As another example, a transposon may be used to introduce a CAR-transporting plasmid and a trans-ferase-transporting plasmid into a target cell. As still another example, the CAR molecule may be added to the genome by a gene editing method (for example, CRISPR/Cas9).

An immune effector cell for preparing an immune effector cell expressing a chimeric antigen receptor (CAR) may be obtained from a subject, and the "subject" includes a living organism (for example, a mammal) in which an immune response can be elicited. Examples of the subject include a human, a dog, a cat, a mouse, a rat, and a transgenic species thereof. T cells may be obtained from numerous sources, including peripheral blood mononuclear cells, bone marrow, lymph node tissue, cord blood, thymic tissue, tissue from a site of infection, ascites, pleural effusion, spleen tissue, and tumors.

The T cells may be obtained from any number of techniques known to those skilled in the art, such as blood units collected from a subject using Ficoll™ separation. Cells from blood are obtained by apheresis or leukapheresis, and an apheresis product typically contains T cells, mononuclear cells, granulocytes, lymphocytes including B cells, other nucleated white blood cells, red blood cells, and platelets.

The cells collected by apheresis may be washed to remove a plasma fraction and to place the cells in an appropriate buffer or medium for subsequent processing steps. T cells are isolated from peripheral blood lymphocytes by lysing the red blood cells and depleting the monocytes, for example, by centrifugation through a PERCOLL™ gradient or by counterflow centrifugation.

Figure 6:
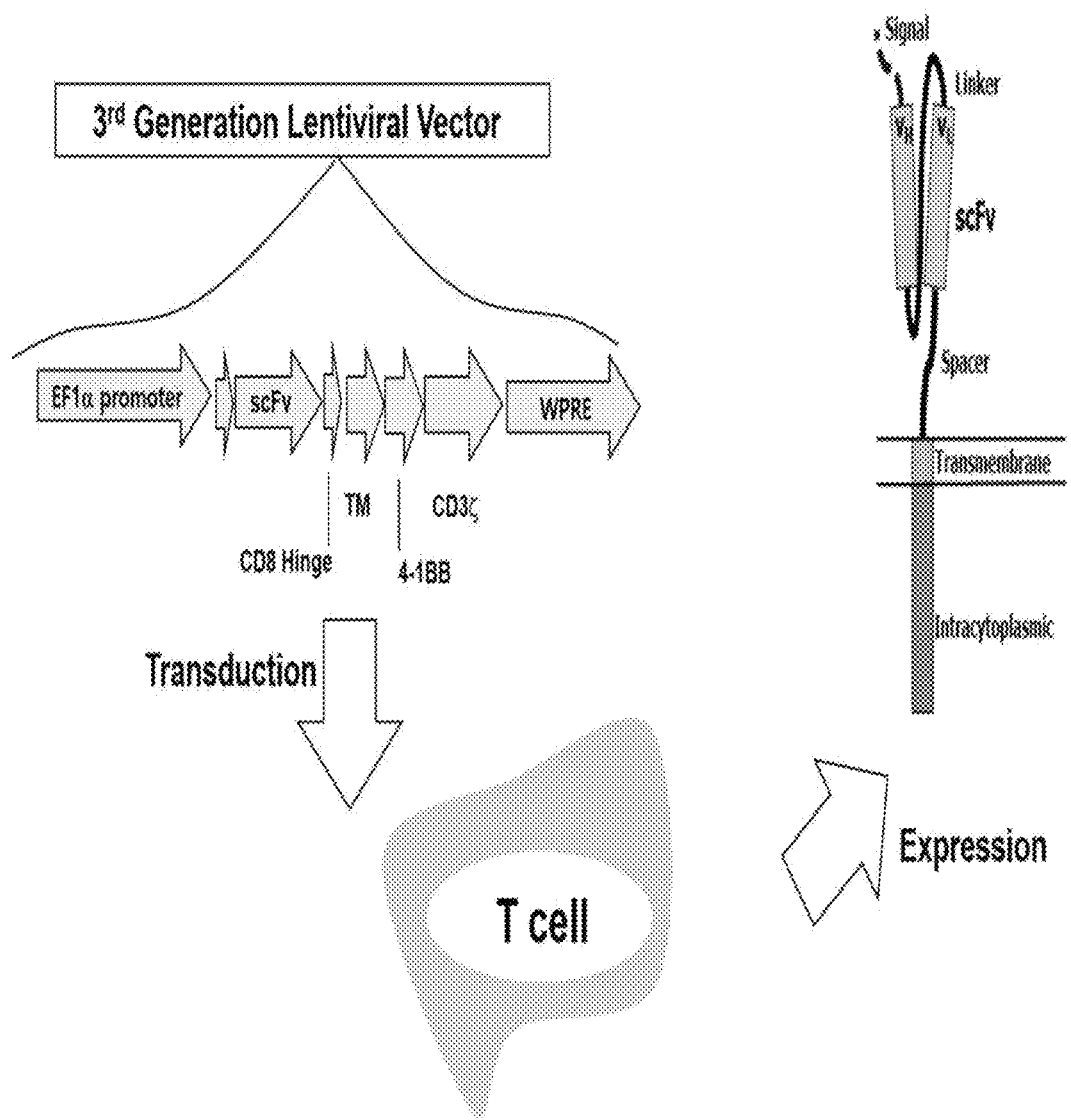
FIG. 6 a schematic view illustrating a method for preparing CD22-CART cells using a lentivirus expressing CD22-CAR.
Figure 7:
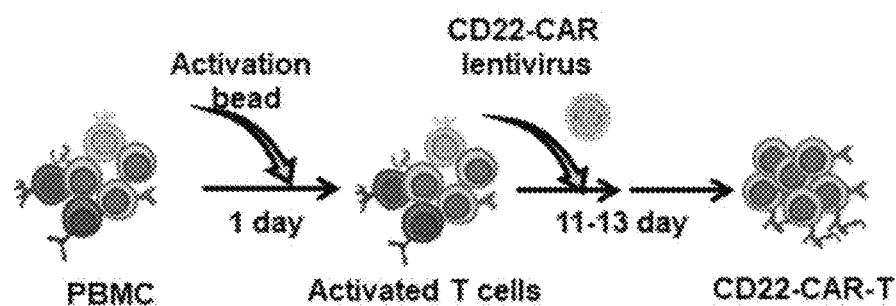
FIG. 7 is a schematic view illustrating (A) a method for preparing CD22-CART cells using peripheral blood mononuclear cells (PBMCs) and (B) a method for confirming the binding ability of the prepared CD22-CAR-T cells to a CD22 peptide.
Figure 7:
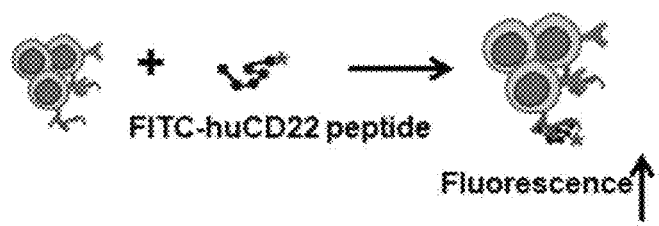

In still another specific exemplary embodiment of the present invention, as illustrated in FIGS. 6 and 7, activated T cells were isolated from peripheral blood monuclear cells (PBMCs), and then CD22-CAR-T cells were prepared by transducing a CD22-CAR lentivirus into T cells, and specifically, CD22-CAR-T cells were prepared using humanized 2G1(V4) and 2G1(V12), respectively.

Figure 8:
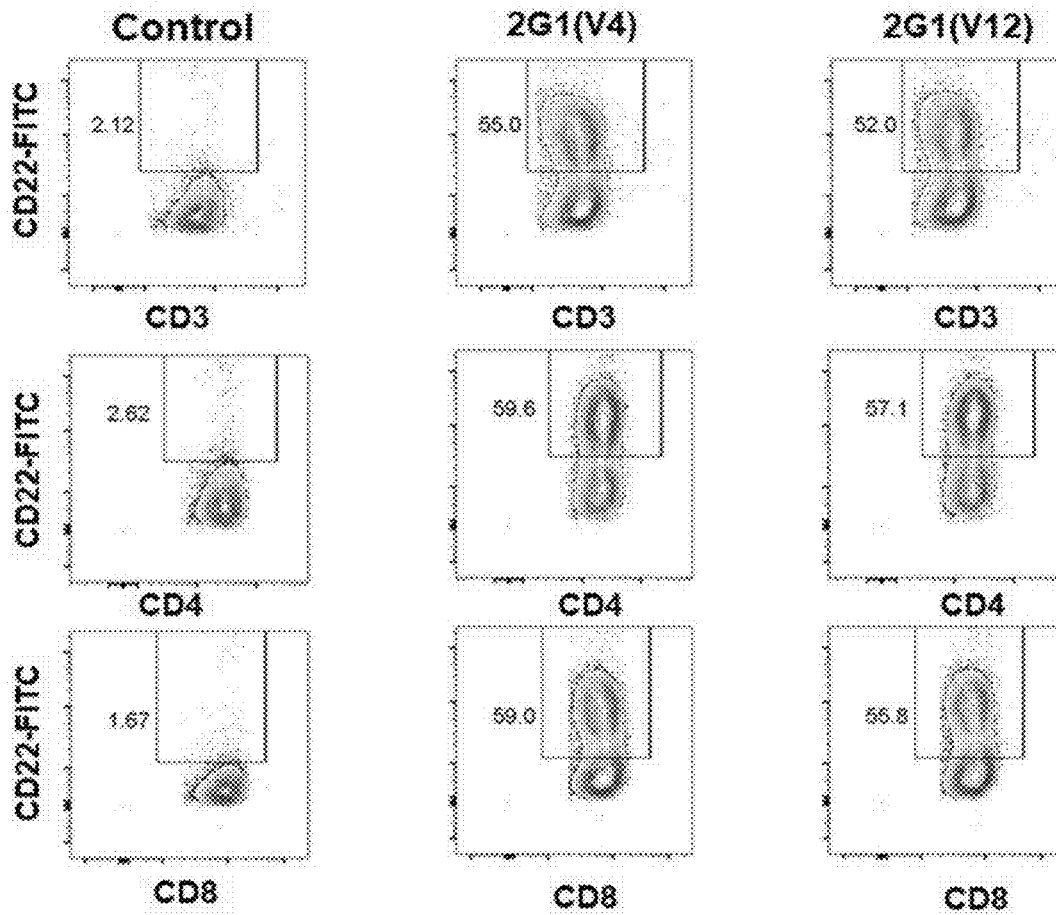
FIG. 8 illustrates the data confirming the CD22 binding ability of 2G1(V4) and 2G1(V12)-based CD22-CAR-T cells, which are humanized anti-CD22 antibodies.

To confirm the activity of the prepared CD22-CAR-T cells, the CD22 peptide binding ability of CD22-CAR-T cells in which CD3, CD4 or CD8 was activated was confirmed. As illustrated in FIG. 8, it was confirmed that the CD22-CAR-T cells prepared in the present invention bound to the CD22 peptide.

Figure 9:
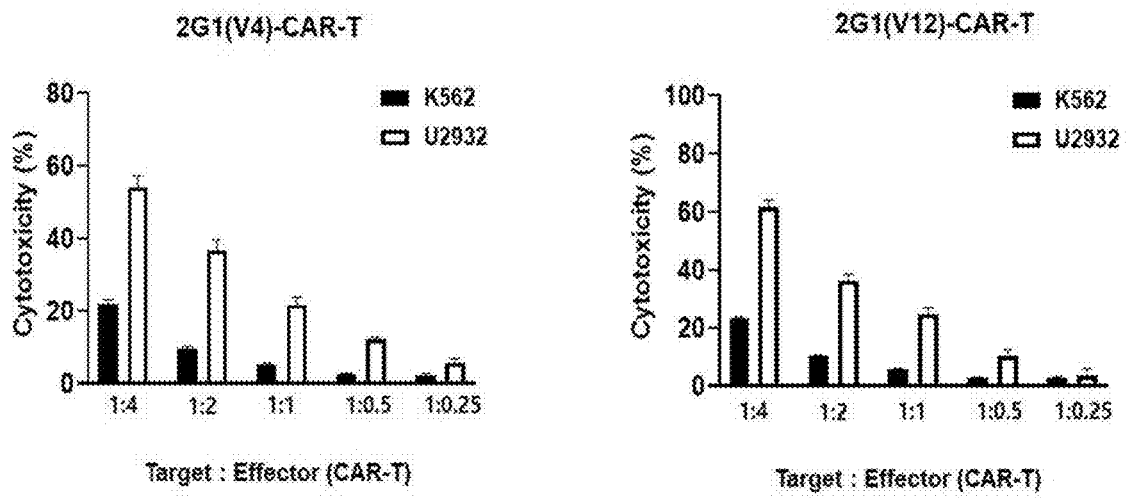
FIG. 9 illustrates the data confirming the apoptotic effects on U2932 cells (CD22-expressing cells) and K562 cells (CD22-non-expressing cells) by 2G1(V4) and 2G1(V12)-based CD22-CAR-T cells, which are humanized anti-CD22 antibodies.

In yet another specific exemplary embodiment of the present invention, as a result of confirming the apoptotic effect on the target cell by the CD22-CAR-T cells, as illustrated in FIG. 9, it was confirmed that the CD22-CAR-T cells specifically exhibited an apoptotic effect on U2932 cells and NALM6 cells expressing CD22.

That is, the humanized anti-CD22 antibody (2G1(V4) and 2G1(V12))-based chimeric antigen receptor of the present invention and CAR-T cells using the same may be usefully used as a composition for preventing or treating a disease related to B cells or CD22 expression.

Bispecific Chimeric Antigen Receptor (CAR) Targeting CD19/CD22

In yet another aspect, the present invention relates to a bispecific antigen receptor targeting CD19 and CD22 (CD19xCD22 bispecific CAR), including:
a CD19-binding domain and a CD22-binding domain;
a transmembrane domain;
a costimulatory domain; and
an intracellular signal transduction domain,
in which the CD22-binding domain is an antibody specifically binding to CD22 or a fragment thereof, including a heavy chain variable region including a CDR1 region represented by an amino acid of SEQ ID: 1, a CDR2 region represented by an amino acid of SEQ ID NO: 2 and a CDR3 region represented by an amino acid of SEQ ID NO: 3 and a light chain variable region including a CDR1 region represented by an amino acid of SEQ ID NO: 4, a CDR2 region represented by an amino acid of SEQ ID NO: 5 and a CDR3 region represented by an amino acid of SEQ ID NO: 6.

In the present invention, the antibody specifically binding to CD22 or the fragment thereof is an anti-CD22 antibody including a heavy chain variable region represented by an amino acid sequence of SEQ ID NO: 7 and a light chain variable region represented by an amino acid sequence of SEQ ID NO: 8, or may be a humanized anti-CD22 antibody including: a heavy chain variable region represented by an amino acid sequence of SEQ ID NO: 11 and a light chain variable region represented by an amino acid sequence of SEQ ID NO: 12; or
a heavy chain variable region represented by an amino acid sequence of SEQ ID NO: 15 and a light chain variable region represented by an amino acid sequence of SEQ ID NO: 16.

In the present invention, the bispecific or bivalent chimeric antigen receptor is a CAR capable of simultaneously binding to two different types of antigens, and in the present invention, preferably, a bispecific chimeric antigen receptor targeting both CD19 and CD22 was prepared, and in the CD19-binding domain, any known anti-CD19 antibody sequence can be used without limitation.

Figure 11:
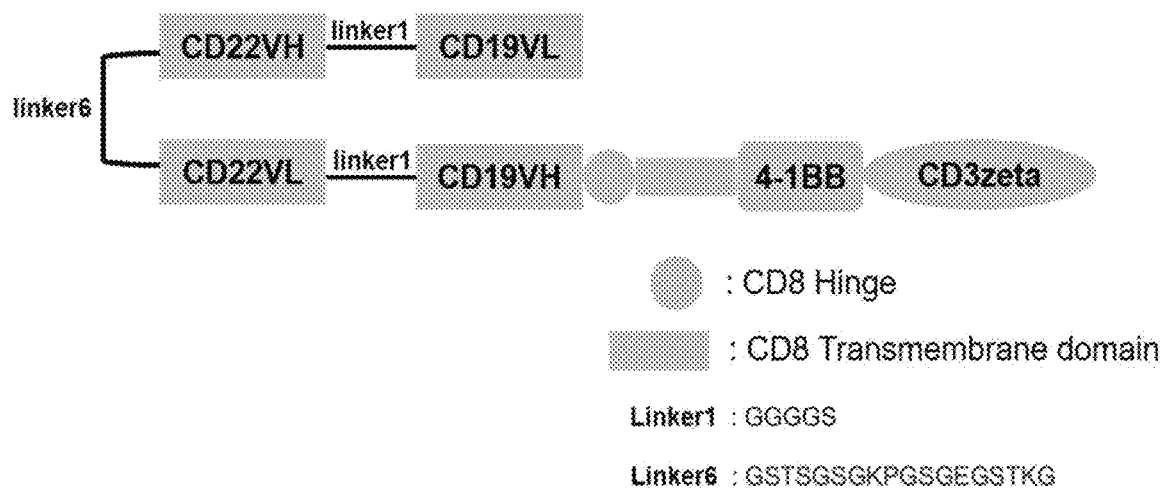
FIG. 11 is a schematic view illustrating a bispecific chimeric antigen receptor (bispecific CAR) targeting CD19 and CD22. Linker1 is the amino acid sequence of SEQ ID NO: 51. Linker6 is the amino acid sequence of SEQ ID NO: 54.

A specific content on the chimeric antigen receptor is as described above, and the CD19-binding domain and CD22-binding domain of the bispecific chimeric antigen receptor were linked in the form of a loop (LoopCAR) as illustrated in FIG. 11. That is, the CD19-binding domain and the CD22-binding domain may be linked in the order of a light chain variable region (CD19VL) of an antibody specifically binding to CD19—a heavy chain variable region (CD22VH) of an antibody specifically binding to CD22—a light chain variable region (CD22VL) of an antibody specifically binding to CD22—a heavy chain variable region (CD19VH) of an antibody specifically binding to CD19.

The light chain variable region of the antibody specifically binding to CD19 may include a CDR1 region represented by an amino acid of SEQ ID NO: 44, a CDR2 region represented by an amino acid of SEQ ID NO: 45 and a CDR3 region represented by an amino acid of SEQ ID NO: 46, and may be preferably represented by an amino acid sequence of SEQ ID NO: 48.

The heavy chain variable region of the antibody specifically binding to CD19 may include a CDR1 region represented by an amino acid of SEQ ID NO: 41, a CDR2 region represented by SEQ ID NO: 42 and a CDR3 region represented by an amino acid of SEQ ID NO: 43, and may be preferably represented by an amino acid sequence of SEQ ID NO: 47.

The CD19-binding domain and the CD22-binding domain may be manufactured by a gene recombination technique so as to be linked by a linker, CD19VL and CD22VH or CD22VL and CD19VH may be preferably linked by a linker (linker 1 in FIG. 11) represented by an amino acid sequence of SEQ ID NO: 51, CD22VH and CD22VL may be linked by a linker (linker 6 in FIG. 11) represented by an amino acid sequence of SEQ ID NO: 54, but the present invention is not limited thereto, and a peptide including any amino acid sequence that does not affect the antibody activity can be used.

Polynucleotide Encoding Bispecific Chimeric Antigen Receptor Targeting CD19/CD22 and Bispecific Chimeric Antigen Receptor Expression Vector Targeting CD19/CD22

In yet another aspect, the present invention relates to a polynucleotide encoding the bispecific chimeric antigen receptor targeting CD19 and CD22.

In the present invention, the polynucleotide encoding the bispecific chimeric antigen receptor may include: a polynucleotide encoding a CD19-binding domain and a polynucleotide encoding a CD22-binding domain; a polynucleotide encoding a transmembrane domain; a polynucleotide encoding a costimulatory domain; and a polynucleotide encoding an intracellular signal transduction domain.

Preferably, the polynucleotide encoding the bispecific chimeric antigen receptor of the present invention may include:
- a bispecific antibody including a light chain variable region (CD19VL; SEQ ID NO: 50) of an antibody specifically binding to CD19—a heavy chain variable region (CD22VH; SEQ ID NO: 9, SEQ ID NO: 13 or SEQ ID NO: 17) of an antibody specifically binding to CD22—a light chain variable region (CD22VL; SEQ ID NO: 10, SEQ ID NO: 14 or SEQ ID NO: 18) of an antibody specifically binding to CD22—a heavy chain variable region (CD19VH; SEQ ID NO: 49) of an antibody specifically binding to CD19;
- a transmembrane domain represented by a base sequence of SEQ ID NO: 32;
- 4-1BB (costimulatory domain) represented by a base sequence of SEQ ID NO: 33; and
- CD3ζ (intracellular signal transduction domain) represented by a base sequence of SEQ ID NO: 34.

When the 'CD19VL and CD22VH' or 'CD22VL and CD19VH' are linked by a linker represented by an amino acid sequence of SEQ ID NO: 51, a polynucleotide for the linker may be represented by a base sequence of SEQ ID NO: 52 or SEQ ID NO: 53, and when the 'CD22VH and CD22VL' are linked by a linker represented by an amino acid sequence of SEQ ID NO: 54, a polynucleotide for the linker may be represented by a base sequence of SEQ ID NO: 55, but the present invention is not limited thereto, and a polynucleotide encoding any amino acid sequence that does not affect the antibody activity can be used.

When a signal peptide is included at the N-terminus of the CD19/CD22-binding domain, a signal peptide represented by a base sequence of SEQ ID NO: 30 may further included. Further, a polynucleotide encoding a hinge region may be further included between the polynucleotide encoding the CD22-binding domain and the transmembrane domain, and may be preferably a CD8 hinge region represented by a base sequence of SEQ ID NO: 31.

In yet another aspect, the present invention relates to a vector including the polynucleotide encoding the bispecific chimeric antigen receptor.

Figure 12:
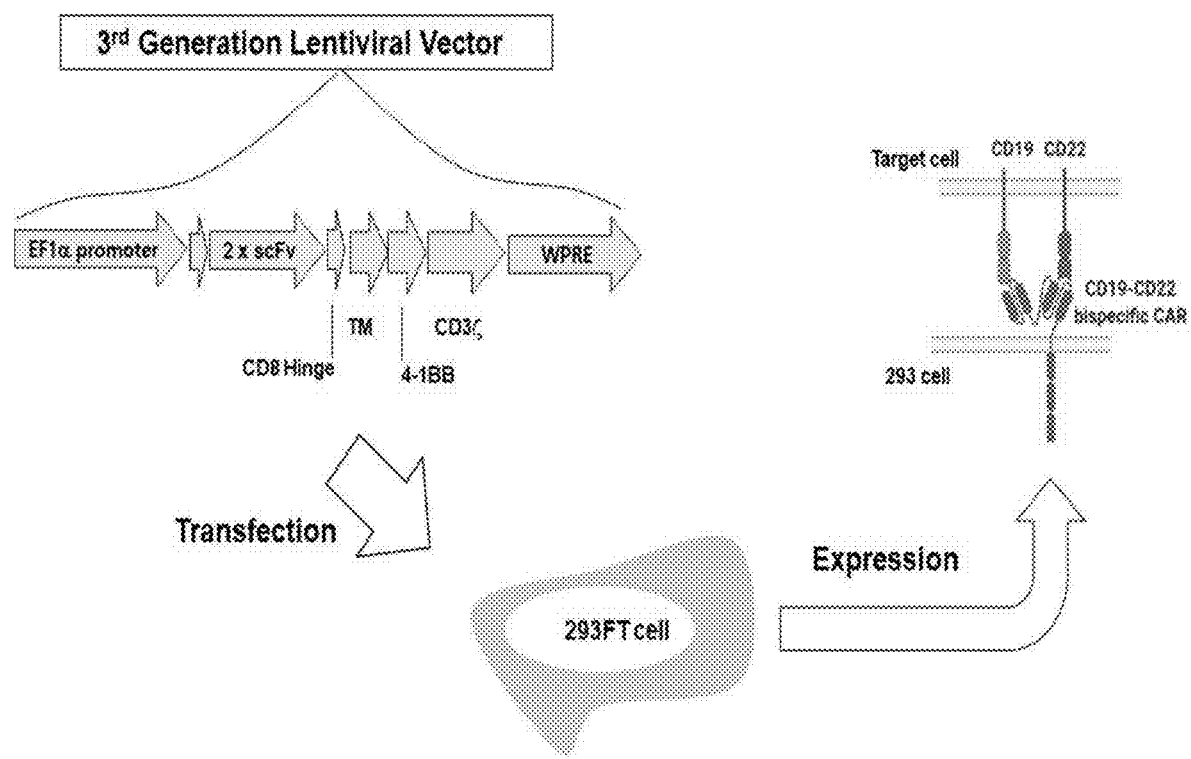
FIG. 12 is a schematic view illustrating a method for preparing CD19xCD22-CAR CD19-expressing cells using a lentivirus expressing bispecific CD19xCD22-CAR targeting CD19 and CD22.

In the present invention, the vector is a recombinant viral vector, preferably, a lentiviral vector, and includes: an operably linked EF1α promoter; a polynucleotide encoding a signal peptide; a polynucleotide encoding a CD19-binding domain and a CD22-binding domain; a polynucleotide encoding a transmembrane domain; and a polynucleotide encoding an intracellular signal transduction domain, and may further include a woodchuck hepatitis virus post-transcriptional regulatory element (WPRE) in order to increase protein expression (FIG. 12).

The EF1α promoter may be represented by a base sequence of SEQ ID NO: 29, and may include a sequence which is 90% or more, 93% or more, 95% or more, 96% or more, 97% or more, 98% or more, or 99% or more identical to the base sequence of SEQ ID NO: 27, if necessary.

In addition, the promoter is operably linked to induce the expression of the anti-CD19/CD22 antibody (CD19VL-CD22VH-CD22VL-CD19VH), which is a CD19xCD22-binding domain, and a specific content on the vector is described above.

Figure 13:
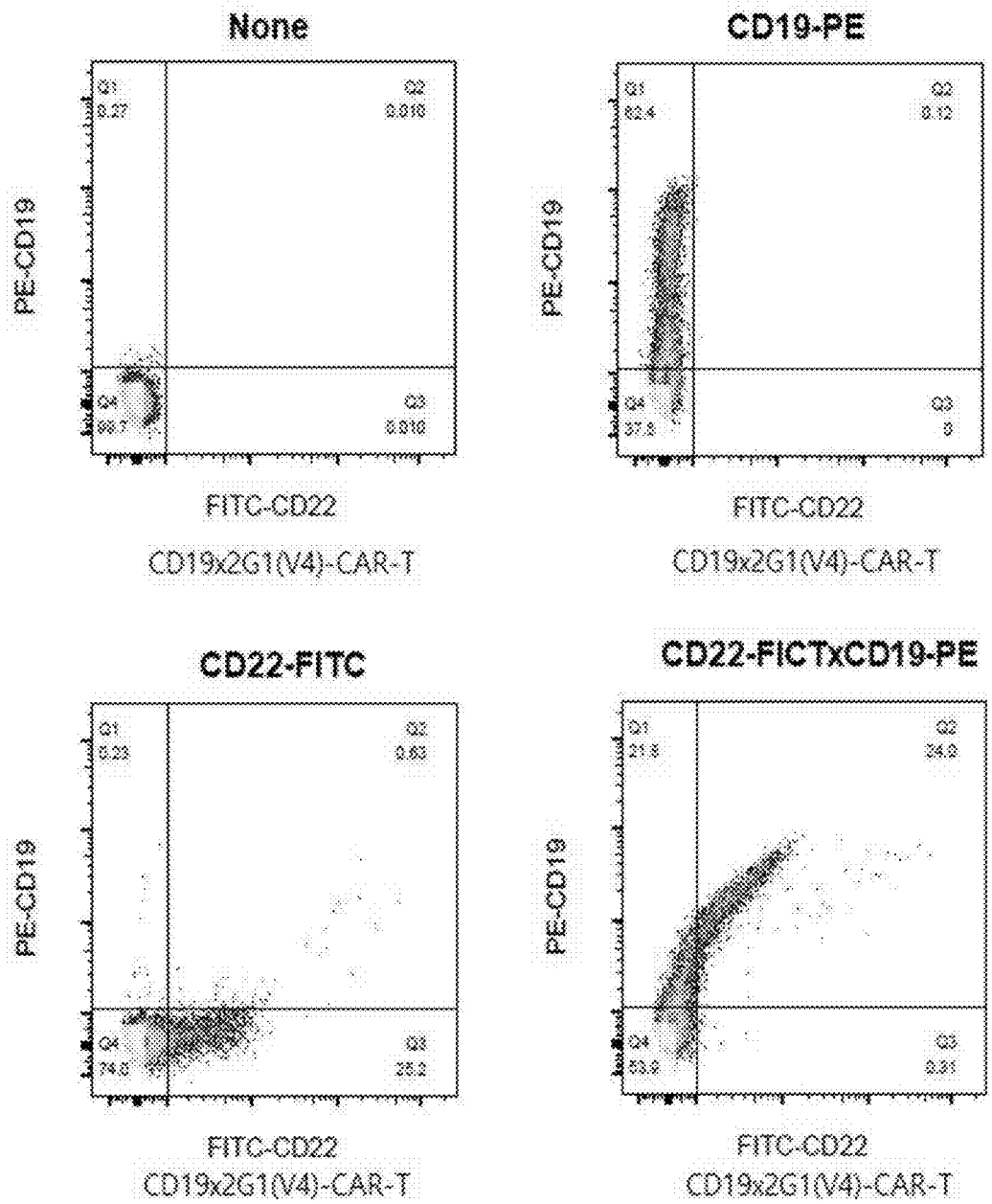
FIG. 13 illustrates the data confirming the expression level of CD19xCD22(V4)-CAR in HEK293FT cells transformed with a lentivirus expressing an anti-CD19 antibody FMC63 and humanized anti-CD22 antibody 2G1(V4)-based CD19xCD22-CAR.
Figure 14:
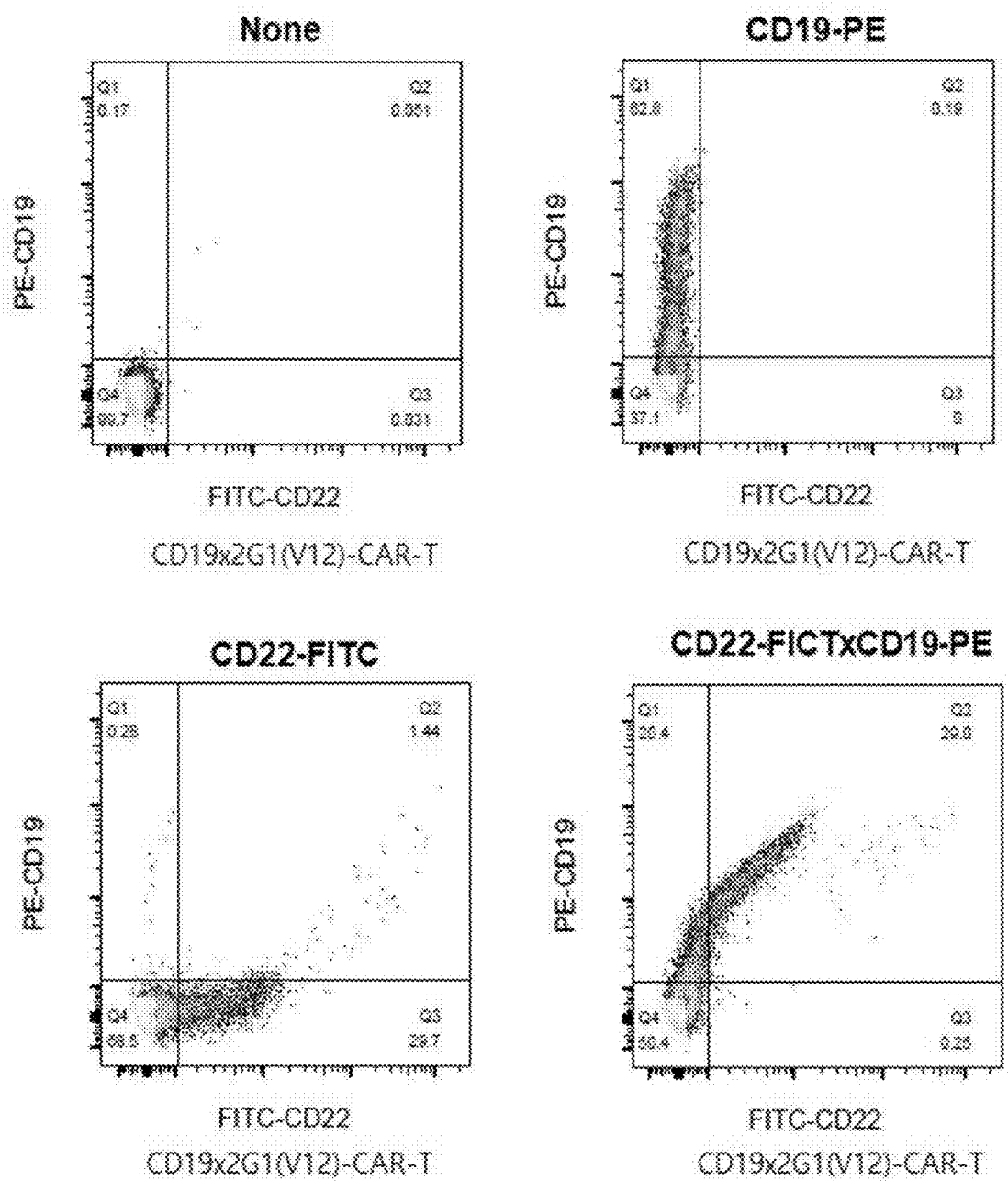
FIG. 14 illustrates the data confirming the expression level of CD19xCD22(V12)-CAR in HEK293FT cells transformed with a lentivirus expressing an anti-CD19 antibody and humanized anti-CD22 antibody 2G1(V12)-based CD19xCD22-CAR(V12).
Figure 15:
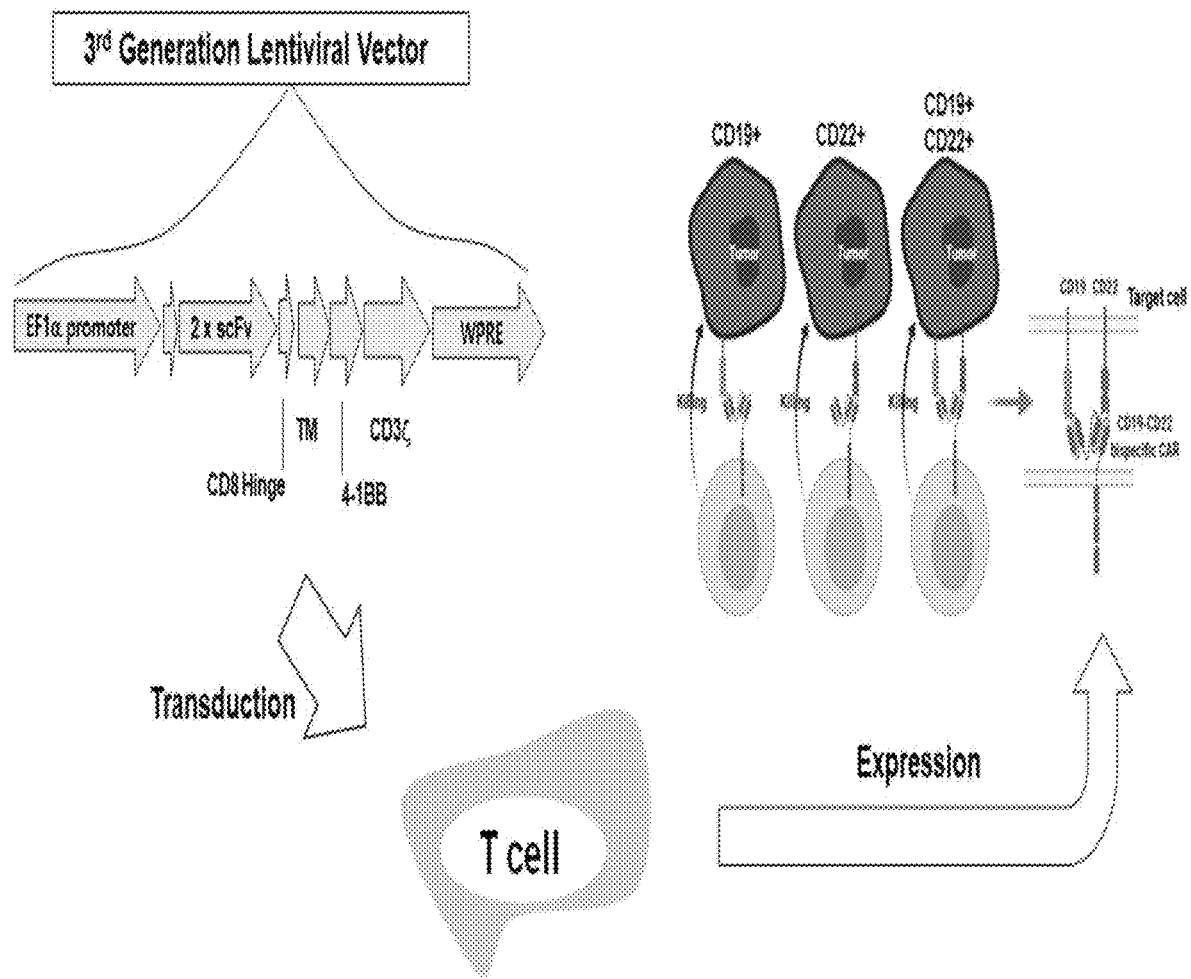
FIG. 15 is a schematic view illustrating a method for preparing CD19xCD22-CAR-T cells using a lentivirus expressing CD19xCD22-CAR.

In a specific exemplary embodiment of the present invention, as illustrated in FIG. 12, a lentiviral vector into which a polynucleotide encoding CD19xCD22-CAR was inserted was prepared, and CD19xCD22-CAR expressing cells were prepared by transforming 293FT cells with the prepared vector. Furthermore, as illustrated in FIGS. 13 and 14, it was confirmed that a bispecific antigen receptor targeting CD19 and CD22 was expressed in the prepared CD19xCD22-CAR expressing cells.

Immune Effector Cell Expressing Bispecific Chimeric Antigen Receptor Targeting CD19xCD22

In yet another aspect, the present invention relates to an immune effector cell, which includes a polynucleotide encoding the bispecific chimeric antigen receptor (CAR) or a vector including the polynucleotide encoding the bispecific chimeric antigen receptor (CAR), and expresses the bispecific chimeric antigen receptor (CAR).

In the present invention, the immune effector cell may be an isolated cell derived from mammals, preferably a T cell, a B cell, a natural killer (NK) cell, a dendritic cell, a bone marrow cell, a mononuclear cell or a macrophage, and more preferably a T cell. Further, a specific content on the chimeric antigen receptor-expressing immune effector cell is as described above.

In a specific exemplary embodiment of the present invention, activated T cells were isolated from peripheral blood mononuclear cells (PBMCs) by the same method as for the preparation of CD22-CAR-T cells (FIG. 7), and then CD19xCD22-CAR-T cells were prepared by transducing a CD19xCD22-CAR lentivirus into T cells, and specifically, CD19xCD22-CAR-T cells were prepared using a 2G1 antibody (mouse), and humanized 2G1(V4) and 2G1(V12), respectively.

Figure 16A:
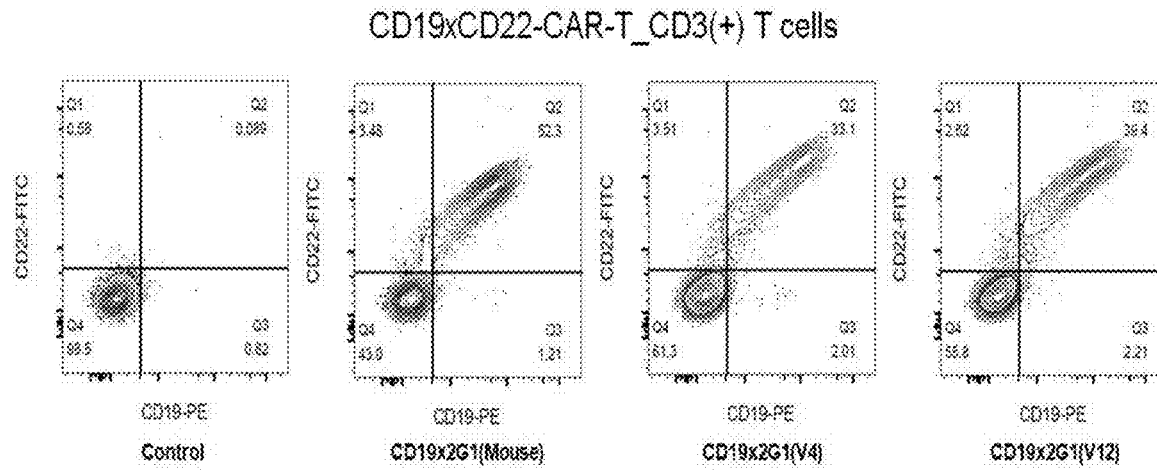
FIGS. 16a-16c illustrate the data confirming the activation of CD19xCD22-CAR-T cells. It was confirmed that in CD3+CD19xCD22-CAR-T cells (A), CD4+CD19xCD22-CAR-T cells (B), and CD8+CD19xCD22-CAR-T cells (C), CD19xCD22-CAR-T cells bound to both a CD22 peptide and a CD19 peptide.
Figure 16B:
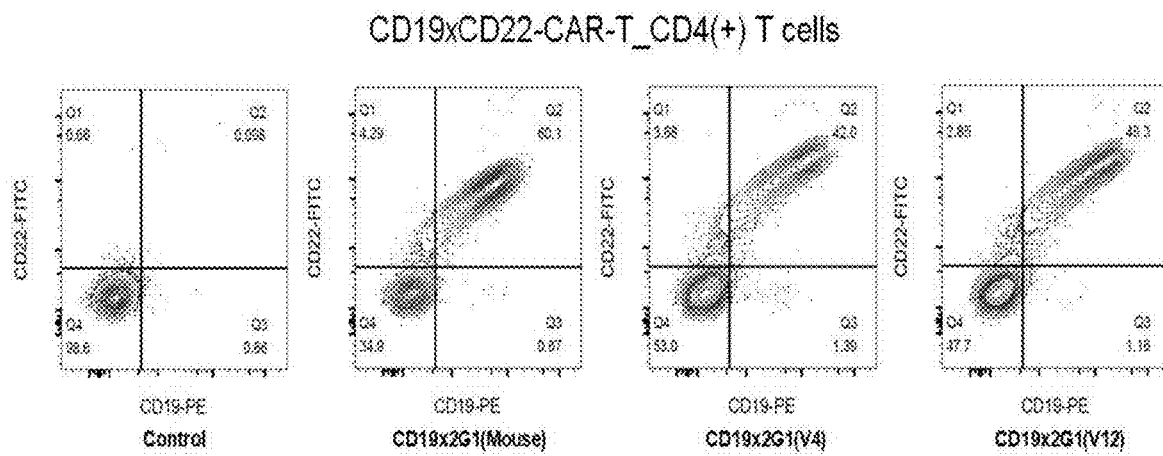
Figure 16C:
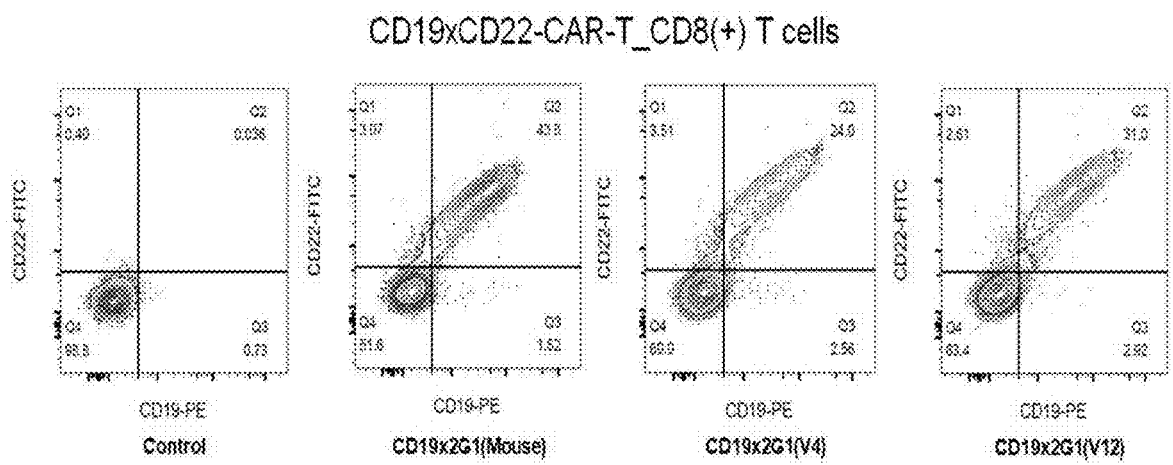

To confirm the activity of the prepared CD19xCD22-CAR-T cells, the CD22 peptide and CD19 peptide binding ability of CD19xCD22-CAR-T cells in which CD3, CD4 or CD8 was activated was confirmed. As illustrated in FIG. 16, it was confirmed that the CD19xCD22-CAR-T cells prepared in the present invention bound to both the CD22 peptide and the CD19 peptide.

Figure 17A:
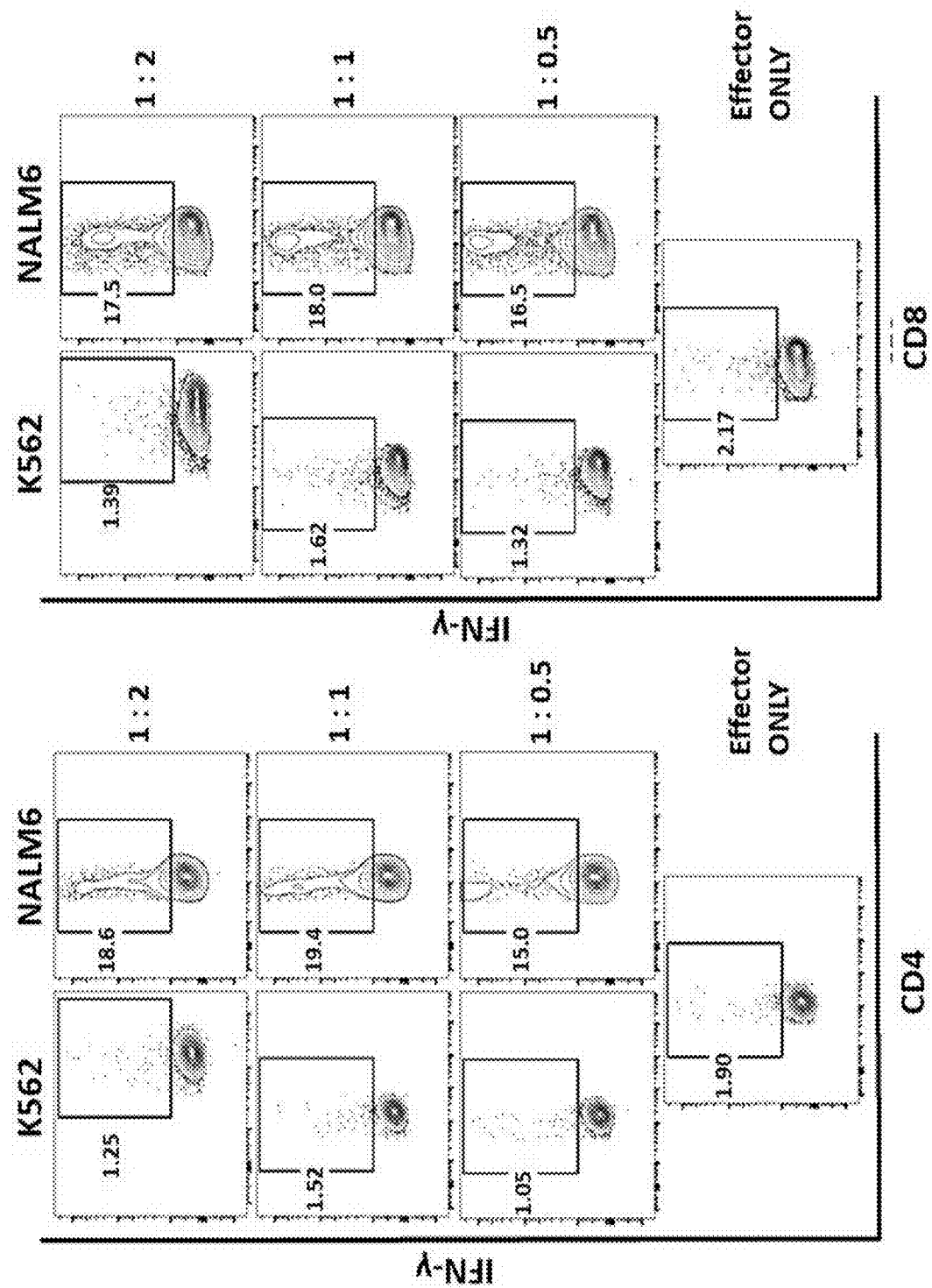
FIGS. 17a-17c illustrate the data confirming the expression level of IFNγ by (A) anti-CD19 antibody and mouse 2G1 antibody-based CD19xCD22(mouse)-CAR-T cells, (B) anti-CD19 antibody and 2G1(V4) antibody-based CD19xCD22(V4)-CAR-T cells, and (C) anti-CD19 antibody and 2G1(V12) antibody-based CD19xCD22(V12)-CAR-T cells in the presence of target cells in order to confirm the activation of CD19xCD22-CAR-T cells.
Figure 17B:
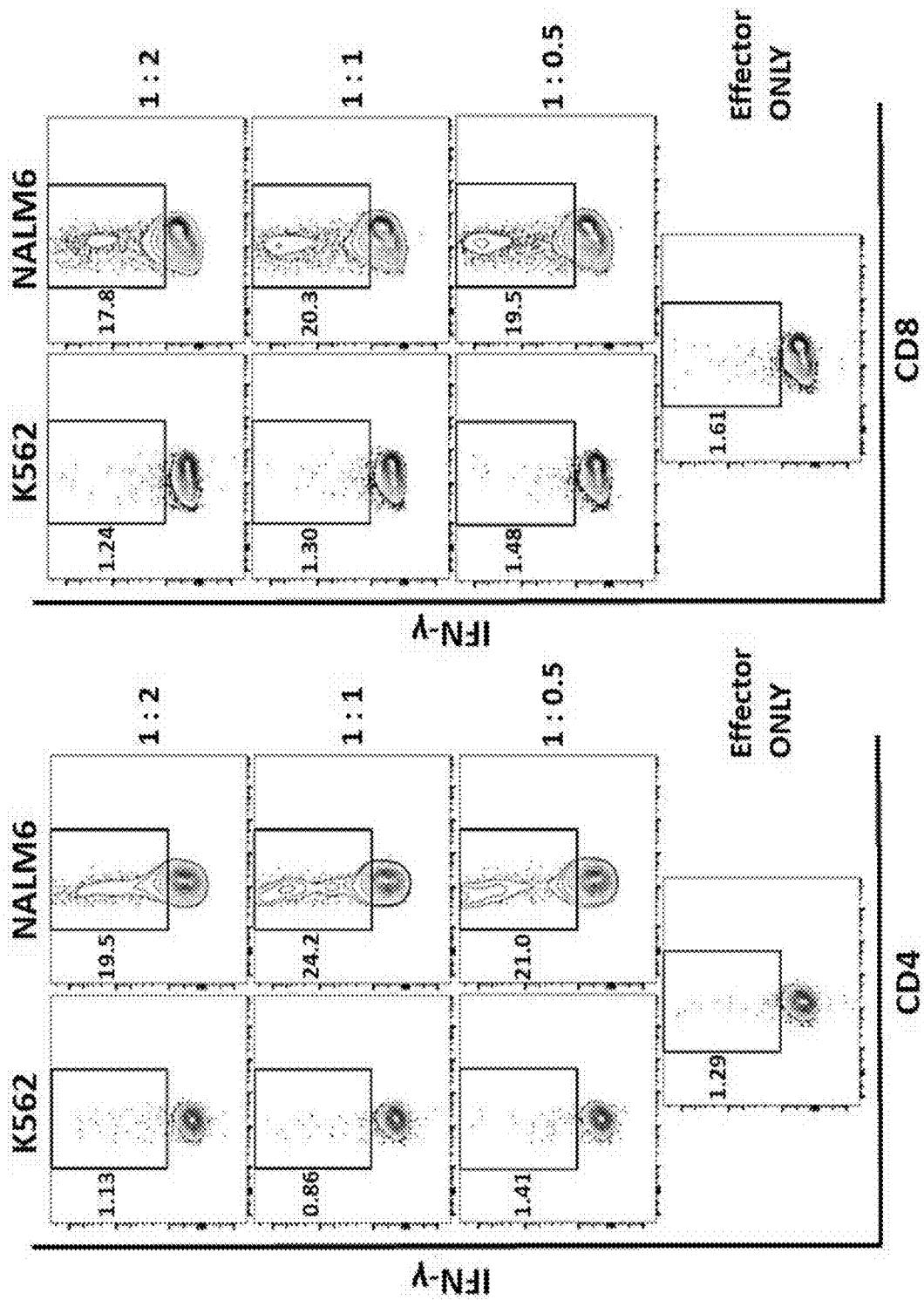
Figure 17C:
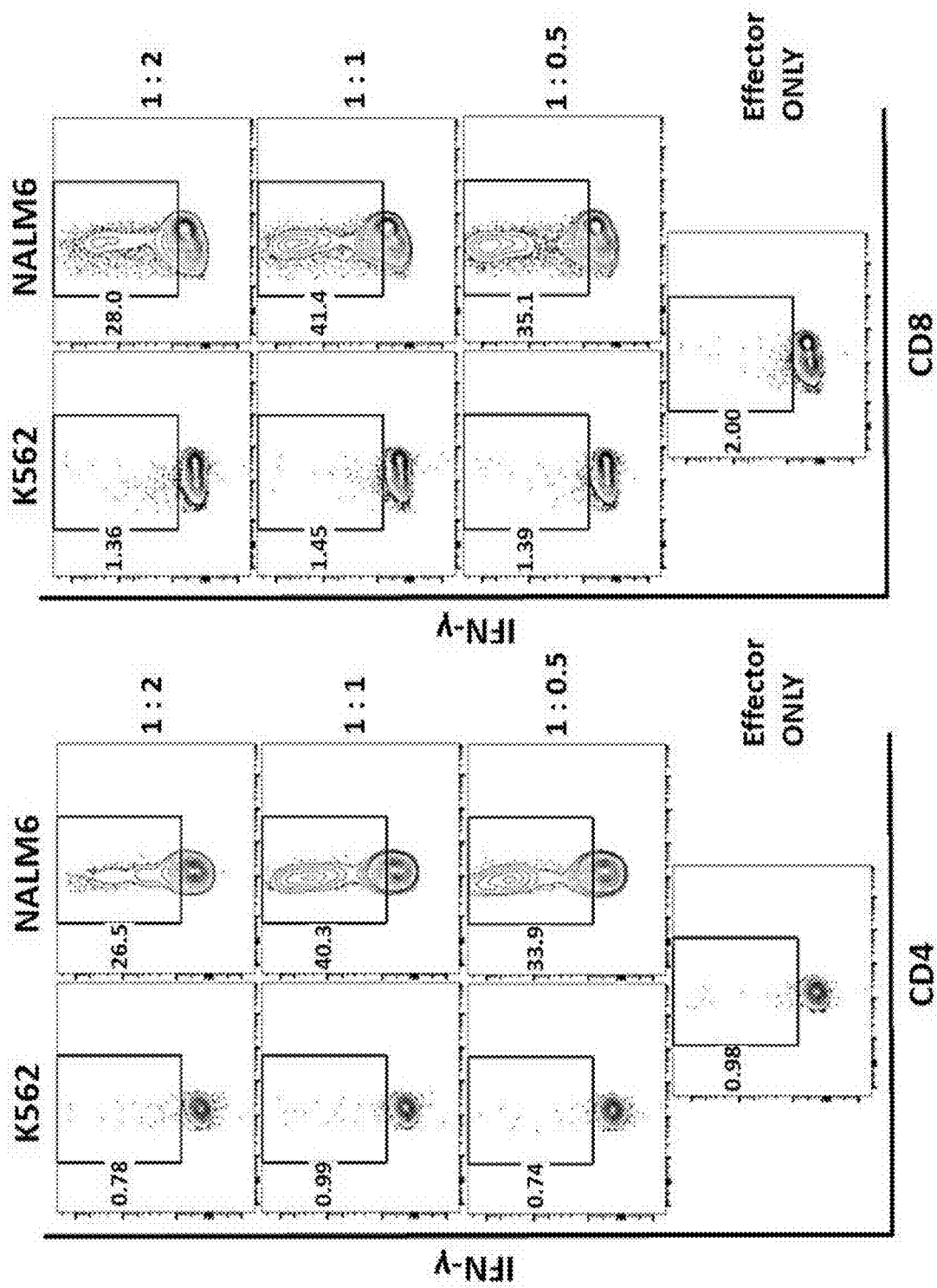

In another specific exemplary embodiment of the present invention, to confirm the activation of CD19xCD22-CAR-T cells, the expression level of IFNγ by CD19xCD22-CAR-T cells was confirmed in the presence of a target cell. As a result, as illustrated in FIGS. 17A to 17C, it was confirmed that T cells were not activated in K562 cells that do not express CD19 and CD22, whereas T cells were activated in the presence of NALM6 cells expressing CD19 and CD22, thereby increasing the expression of IFNγ.

In another specific exemplary embodiment of the present invention, as a result of confirming the apoptotic effect on the target cell by the CD19xCD22-CAR-T cells, as illustrated in FIG. 18, it was confirmed that the CD19xCD22-CAR-T cells specifically exhibited an apoptotic effect on NALM6 cells expressing CD19 and CD22.

Furthermore, in still another specific exemplary embodiment of the present invention, to confirm the antitumor effects of CD19xCD22-CAR-T cells, CD19xCD22-CAR-T cells prepared using a humanized 2G1-V4 antibody were injected intratumorally into a mouse model xenografted with tumor cells, and then changes in tumor size were observed. As a result, as illustrated in FIG. 19, it was confirmed that the antitumor effects of the CD19xCD22-CAR-T cells of the present invention were excellent compared to those of antibody-based palivizumab-CAR-T cells binding to the SV40 virus used as a positive control, and it was confirmed that when CD19xCD22-CAR-T cells were treated at 5×10$^6$ or more, most of the tumor cells were killed, and thus no tumor tissue was observed.

That is, the bispecific chimeric antigen receptor targeting the CD19xCD22 of the present invention and CD19xCD22-

CAR-T cells may be usefully used as a composition for preventing or treating a disease related to B cells or CD19xCD22 expression.

Composition for Preventing or Treating Disease Mediated by B Cells or Disease Mediated by CD19xCD22 Expression In yet another aspect, the present invention relates to a pharmaceutical composition for preventing or treating a disease mediated by B cells, including: a humanized antibody specifically binding to CD22; an immune effector cell expressing a chimeric antigen receptor targeting CD22; or an immune effector cell expressing a bispecific chimeric antigen receptor specifically binding to CD19xCD22.

In the present invention, the B cells may be preferably cells expressing CD19 or CD22, and the disease may be selected from the group consisting of tumors/cancer, lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma (SLL), leukemia, hairy cell leukemia (HCL), acute lymphocytic leukemia (ALL), Burkitt's lymphoma and mantle cell lymphoma.

In the present invention, the composition may include a therapeutic agent for a disease mediated by B cells, and the therapeutic agent may be present in a covalently bound state to an antibody specifically binding to CD19 or CD22, or may be administered in combination with the CD22-CAR immune effector cell or CD19xCD22-CAR immune effector cell of the present invention.

The therapeutic agent includes a small molecule drug, a peptidic drug, a toxin (for example, a cytotoxin), and the like.

The small molecule drug exhibits the pharmaceutical activity of a drug of interest and may generally be a compound having a molecular weight of about 800 Da or less or 2000 Da or less. An inorganic small molecule refers to a molecule that does not contain any carbon atoms, whereas an organic small molecule refers to a compound that contains at least one carbon atom.

The peptidic drug refers to an amino acid containing a polymeric compound, and includes naturally occurring and non-naturally occurring peptides, oligopeptides, cyclic peptides, polypeptides and proteins, as well as peptide mimetics. The peptide drug may be obtained by chemical synthesis or may be produced from a genetically encoded source (for example, a recombinant source). The peptide drug may have a molecular weight ranging from 200 Da to 10 kDa or more.

The toxin is preferably a cytotoxin, and non-limiting examples of the cytotoxin include ricin, abrin, diphtheria toxin, Pseudomonas exotoxin (for example, PE35, PE37, PE38, PE40, and the like), saporin, gelonin, pokeweed antiviral protein (PAP), botulinum toxin, bryodin, momordin and bouganin.

Further, the therapeutic agent may be an anticancer agent. The anticancer agent includes a non-peptidic (that is, non-protein-based) compound which reduces the proliferation of cancer cells and encompasses a cytotoxic drug and a cell proliferation inhibitor. Non-limiting examples of the anticancer agent include an alkylating agent, a nitrosourea, an antimetabolite, an anti-tumor antibiotic, a plant (vinca) alkaloid and a steroid hormone. A peptidic compound may also be used.

The humanized antibody, CD22-CAR immune effector cell or CD19xCD22-CAR immune effector cell specifically binding to CD22 in the pharmaceutical composition is the only active ingredient in the therapeutic or diagnostic composition, or can be used together with, for example, other antibody ingredients such as anti-T cells, and anti-IFNγ or anti-LPS antibodies, or other active ingredients including non-antibody ingredients such as xanthine.

The drug composition preferably includes a therapeutically effective amount of the antibody of the invention. As used herein, the term "therapeutically effective amount" refers to an amount of therapeutic agent required to treat, ameliorate or prevent a target disease or condition, or refers to an amount of therapeutic agent required to exhibit an appreciable therapeutic or prophylactic effect. For any antibody, the therapeutically effective dosage may be initially determined by cell culture assays or by animal models, usually rodents, rabbits, dogs, pigs or primates. Animal models may also be used to determine the appropriate concentration range and route of administration. This information may be used to determine useful dosages and routes for dosing in humans.

A precise effective amount for human patients may depend on the severity of the disease state, the general health status of the patient, the age, body weight and gender of the patient, the diet, the time of administration, the frequency of administration, the composition of the drug, the sensitivity of the reaction and the tolerance/response to the treatment. The amount may be determined by routine experimentation and is within the judgment of a clinician. In general, the effective dosage is 0.01 to 50 mg/kg, preferably 0.1 to 20 mg/kg, and more preferably about 15 mg/kg.

The composition may be administered individually to the patient, or may be administered in combination with other preparations, drugs or hormones.

The dosage at which the antibody of the present invention is administered depends on the nature of the condition to be treated, the grade of malignant lymphoma or leukemia, and whether the antibody is used to prevent disease or to treat an existing condition.

The frequency of administration depends on the half-life of the antibody molecule and the duration of the drug effect. When the antibody molecule has a short half-life (for example, 2 to 10 hours), it may be necessary to provide one or more doses per day. Alternatively, when the antibody molecule has a long half-life (for example, 2 to 15 days), it may be necessary to provide a dose once a day, once a week, or once every 1 or 2 months.

In addition, the pharmaceutical composition may contain a pharmaceutically acceptable carrier for administration of the antibody. The carrier itself should not cause the production of antibodies harmful to the individual to which the composition is administered, and should be non-toxic. Suitable carriers may be slowly metabolized macromolecules, such as proteins, polypeptides, liposomes, polysaccharides, polylactic acid, polyglycolic acid, amino acid polymers, amino acid copolymers and inactive viral particles.

Pharmaceutically acceptable salts are, for example, mineral acid salts such as hydrochloride, hydrobromide, phosphate and sulfate, or salts of organic acids such as acetic acid, propionic acid, malonic acid and benzoic acid may be used.

Pharmaceutically acceptable carriers in the therapeutic composition may additionally include liquids such as water, saline, glycerol and ethanol. Additionally, auxiliary substances such as wetting agents, emulsifying agents or pH buffering agents may be present in such compositions. The carrier may be formulated as tablets, pills, dragees, capsules, liquids, gels, syrups, slurries, and suspensions for ingestion of the pharmaceutical composition by the patient.

Preferred forms for administration include forms suitable for parenteral administration, for example by injection or infusion (for example, bolus injection or continuous infusion). When the product is for infusion or injection, it may take the form of a suspension, solution or emulsion in an oil or water-soluble excipient, which may include formulations such as suspending agents, preservatives, stabilizers and/or dispersants. Alternatively, the antibody molecule may be in anhydrous form, and may be reconstituted with an appropriate sterile solution before use.

Once formulated, the compositions of the present invention can be administered directly to a patient. Patients to be treated may be animals. However, it is preferred that the composition is tailored for administration to human patients.

The pharmaceutical composition of the present invention is not limited, but may be administered by any route including oral, intravenous, intramuscular, intraarterial, intramedullary, intrathecal, intraventricular, transdermal, transcutaneous (for example, see WO 98/20734, incorporated herein by reference), subcutaneous, intraperitoneal, intranasal, intestinal, topical, sublingual, vaginal or rectal routes. A hypospray may be used to administer the pharmaceutical composition of the present invention. Typically, the therapeutic composition may be prepared as an injectable material as a liquid solution or suspension. In addition, solid forms suitable for liquid excipient solutions or suspensions may be prepared prior to injection.

The direct delivery of the composition may generally be achieved by injection, subcutaneous injection, intraperitoneal injection, intravenous injection, or intramuscular injection, or may also be delivered to the interstitial space of the tissue. Furthermore, the composition may be administered to a wound site. Dosage treatment may be a single dosing schedule or multiple dosing schedules.

The active ingredient in the composition may be an antibody molecule. As such, it can be susceptible to degradation in the gastrointestinal tract. Therefore, when the composition is administered by a route using the gastrointestinal tract, the composition will need to contain an agent that protects the antibody from degradation but releases the antibody once absorbed from the gastrointestinal tract.

A complete discussion of pharmaceutically acceptable carriers is available in Remington's Pharmaceutical Sciences (Mack Publishing Company, NJ, 1991).

Hereinafter, preferred examples for helping the understanding of the present invention will be suggested. However, the following examples are provided only to more easily understand the present invention, and the contents of the present invention are not limited by the following examples.

[Example 1]
Preparation and Selection of Antibody Specifically Binding to CD22

In order to select an antibody specific for a CD22 peptide, a hybridoma that produces an antibody binding to CD22 was prepared to select the antibody.

First, spleen cells were excised by immunizing a CD22 protein (ACRObiosystems Inc., cat #CD2-H52H8, USA), and hybridoma cells were produced through cell fusion with mouse myeloma cells.

Mouse myeloma cells used for cell fusion cannot survive in the HAT medium because they do not have the Hypoxanthine Guanidine-Phosphoribosyl-Transforase (HGPRT) gene, but hybridomas can survive in the HAT medium by fusion with spleen cells. Since only hybridomas can be proliferated using the HAT medium, hybridomas are typically b in the HAT medium until the hybridomas are established.

A limiting dilution method was used to select a hybridoma that produces an antibody binding to CD22 from among the proliferated hybridomas. First, the number of cells was reduced to 1 cell or less per 96 wells, and then it was confirmed by ELISA whether an antibody obtained from a clone proliferated from one cell bound to CD22, and a clone binding to CD22 was selected. The above process was repeated three times to select hybridomas that produced the antibody binding to CD22. The antibody binding to CD22 was obtained in this manner.

The antibody is named 2G1 and these base sequences and amino acid sequences were analyzed. The sequence information on the heavy chain variable region and light chain variable region of each antibody according to the sequence analysis results is shown in the following Table 1, and the underlined part in Table 1 means a complementarity determining region (CDR).

TABLE 1

Sequence information of 2G1 antibody

| 2G1 | Sequence information | SEQ ID NO |
|---|---|---|
| Heavy chain variable region CDR1 | GFSLTSYDI | SEQ ID NO: 1 |
| Heavy chain variable region CDR2 | IWTGGGT | SEQ ID NO: 2 |
| Heavy chain variable region CDR3 | VPHYYGYAMDYW | SEQ ID NO: 3 |
| Light chain variable region CDR1 | QDINKY | SEQ ID NO: 4 |
| Light chain variable site CDR2 | YTS | SEQ ID NO: 5 |
| Light chain variable site CDR3 | LQYDNLLT | SEQ ID NO: 6 |

TABLE 1-continued

Sequence information of 2G1 antibody

| 2G1 | Sequence information | SEQ ID NO |
|---|---|---|
| Heavy chain variable region amino acid sequence | EVQLQESGPGLVAPSQSLSITCTVSGFSLTSYDISWIRQPPGKGLEWLGVIWTGGGTNYNSAFMSRLSISKDNSKSQVFLKMSSLQTDDTAIYYCVPHYYGYAMDYWGQGTSVTVSS | SEQ ID NO: 7 |
| Light chain variable region amino acid sequence | DIVLTQSPSSLSASLGGKVTITCKASQDINKYIAWYQHKPGKGPRLLIHYTSTLQPGIRSRFSGSGSGRDYSFSISNLEPEDIATYYCLQYDNLLTFGAGTKLELK | SEQ ID NO: 8 |
| Heavy chain variable region base sequence | GAGGTGCAGCTGCAGGAGTCAGGACCTGGCCTGGTGGCGCCCTCACAGAGCCTGTCCATTACCTGCACTGTCTCTGGGTTCTCATTAACCAGCTATGATATAAGCTGGATTCGCCAGCCACCAGGAAAGGGTCTGGAGTGGCTTGGAGTAATATGGACTGGTGGAGGCACAAATTATAATTCAGCTTTCATGTCCAGACTGAGCATCAGCAAGGACAACTCCAAGAGCCAAGTTTTCTTAAAAATGAACAGTCTGCAAACTGATGACACAGCCATATATTACTGTGTCCCTCATTACTACGGCTATGCTATGGACTACTGGGGTCAAGGAACCTCAGTCACCGTCTCCTCA | SEQ ID NO: 9 |
| Light chain variable region base sequence | GATATTGTGCTGACCCAGTCTCCATCCTCACTGTCTGCATCTCTGGGAGGCAAAGTCACCATCACTTGCAAGGCAAGCCAAGACATTAACAAGTATATAGCTTGGTACCAACAAGCCTGGAAAAGGTCCTAGGCTGCTCATACATTACACATCTACATTACAGCCAGGCATCCCATCAAGGTTCAGTGGAAGTGGGTCTGGGAGAGATTATTCCTTCAGCATCAGCAACCTGGAGCCTGAAGATATTGCAACTTATTATTGTCTACAGTATGATAATCTGCTCACGTTCGGTGCTGGGACCAAGCTGGAGCTGAAA | SEQ ID NO: 10 |

[Example 2]
Preparation of 2G1 Antibody-Based Humanized Antibody

A humanized antibody in which the 2G1 antibody selected in Example 1 was changed to a structure corresponding to humans was prepared.

Specifically, mouse 2G1 antibodies were constructed into humanized antibodies by a CDR grafting method of replacing the CDR of a mouse antibody binding to CD22 with the CDR of a human antibody using a germline sequence of a human antibody as a frame. The humanized antibodies were named 2G1(V4) and 2G1(V12) and their amino acid sequences were analyzed. The sequence information on the heavy chain variable region and light chain variable region of the antibodies according to the sequence analysis results is shown in the following Tables 2 and 3, and the underlined parts in Tables 2 and 3 mean complementarity determining regions (CDRs).

TABLE 2

Sequence information of 2G1(V4) antibody

| 2G1-V4 | Sequence information | SEQ ID NO |
|---|---|---|
| Heavy chain variable region CDR1 | GFSLTSYDI | SEQ ID NO: 1 |
| Heavy chain variable region CDR2 | IWTGGGT | SEQ ID NO: 2 |
| Heavy chain variable region CDR3 | VPHYYGYAMDYW | SEQ ID NO: 3 |
| Light chain variable region CDR1 | QDINKY | SEQ ID NO: 4 |
| Light chain variable region CDR2 | YTS | SEQ ID NO: 5 |
| Light chain variable region CDR3 | LQYDNLLT | SEQ ID NO: 6 |

TABLE 2-continued

Sequence information of 2G1(V4) antibody

| 2G1-V4 | Sequence information | SEQ ID NO |
|---|---|---|
| Heavy chain variable region amino acid sequence | EVQLQESGPGLVKPSQTLSLTCTVSGFSLTSYDI SWIRQPPGKGLEWLGVIWTGGGTNYNSALKSRVT ISKDNSKSQVSLKLSSVTAADTAVYYCVPHYYGY AMDYWGQGTTVTVSS | SEQ ID NO: 11 |
| Light chain variable region amino acid sequence | EIVLTQSPATLSLSPGERATLSCRASQDINKYIA WYQQKPGQAPRLLIHYTSTRQTGIPARFSGSGSG RDYTLTISSLEPEDFAVYYCLQYDNLLTFGGGTK LEIK | SEQ ID NO: 12 |
| Heavy chain variable region base sequence | GAGGTGCAGCTGCAGGAGAGCGGCCCCGGCCTGG TGAAGCCGAGCCAGACTCTTTCTCTGACCTGCAC CGTGTCCGGCTTCTCTCTTACGAGCTACGACATC TCGTGGATCCGGCAGCCGCCTGGGAAAGGCTTAG AGTGGCTAGGGGTGATTTGGACCGGCGGGGGTAC CAACTACAACTCCGCGCTCAAATCCCGCGTCACT ATTTCTAAGGACAATTCCAAGAGCCAGGTCTCGC TGAAGCTCTCGTCCGTGACCGCCGCGGACACCGC AGTTTATTACTGCGTGCCTCATTACTACGGCTAC GCCATGGATTATTGGGGCCAGGGCACCACAGTAA CAGTCAGCTCC | SEQ ID NO: 13 |
| Light chain variable region base sequence | GAGATCGTGCTGACTCAGAGCCCGGCCACCCTTA GCCTGAGTCCAGGCGAGCGCGCTACGTTGTCATG CCCGAGCTTCCCAGGACATTAACAAGTACATCGCG TGGTACCAGCAGAAGCCCGGACAGGCCCCCCGCC TGCTCATCCACTACACCTCCACCCGCCAGACTGG CATCCCTGCCAGGTTTTCAGGCTCCGGTTCTGGC CGTGACTACACCCTGACCATCTCTAGTTTGGAGC CCGAAGATTTCGCCGTGTACTACTGTCTGCAATA TGACAACCTGCTGACCTTCGGAGGGGGTACCAAG CTGGAGATCAAG | SEQ ID NO: 14 |

TABLE 3

Sequence information of 2G1(V12) antibody

| 2G1-V12 | Sequence information | SEQ ID NO |
|---|---|---|
| Heavy chain variable region CDR1 | GFSLTSYDI | SEQ ID NO: 1 |
| Heavy chain variable region CDR2 | IWTGGGT | SEQ ID NO: 2 |
| Heavy chain variable region CDR3 | VPHYYGYAMDYW | SEQ ID NO: 3 |
| Light chain variable region CDR1 | QDINKY | SEQ ID NO: 4 |
| Light chain variable region CDR2 | YTS | SEQ ID NO: 5 |
| Light chain variable region CDR3 | LQYDNLLT | SEQ ID NO: 6 |
| Heavy chain variable region amino acid sequence | EVQLKESGPVLVKPTETLTLTCTVSGFSLTSYDI SWIRQPPGKALEWLGVIWTGGGTNYNSALKSRLT ISKDNSKSQVVLTMTNMDPVDTATYYCVPHYYGY AMDYWGQGTTVTVSS | SEQ ID NO: 15 |
| Light chain variable region amino acid sequence | EIVLTQSPATLSLSPGERATLSCRASQDINKYIA WYQQKPGQAPRLLIHYTSTRQTGIPARFSGSGSG RDYTLTISSLEPEDFAVYYCLQYDNLLTFGGGTK LEIK | SEQ ID NO: 16 |

TABLE 3-continued

Sequence information of 2G1(V12) antibody

| 2G1-V12 | Sequence information | SEQ ID NO |
|---|---|---|
| Heavy chain variable region base sequence | GAGGTGCAGCTGAAGGAGAGCGGGCCGGTGCTGG<br>TGAAGCCTACCGAGACTCTGACCCTGACCTGCAC<br>TGTTTCCGGCTTCTCTCTGACGAGCTACGACATC<br>AGTTGGATCCGCCAGCCACCCGGCAAAGCGTTGG<br>AATGGCTCTGGGGTAATTTGGACCGGTGGCGGGA<br>CCAACTACAACAGCGCGCTCAAATCGCGGCTAAC<br>CATCTCAAAGGACAACTCCAAGTCCCAAGTGGTG<br>TTAACTATGACAAATATGGATCCGGTCGACACCG<br>CTACCTATTACTGCGTGCCTCATTACTACGGCTA<br>CGCCATGGATTATTGGGGCCAGGGCACGACCGTG<br>ACCGTCTCCAGT | SEQ ID NO: 17 |
| Light chain variable region base sequence | GAGATCGTGTTGACCCAGAGCCCTGCCACGCTGA<br>GCCTGTCCCCGGGGAGCGCGCCACTCTTTCGTG<br>TAGGGCTTCCCAGGACATTAACAAGTACATCGCA<br>TGGTACCAGCAGAAGCCCGGACAGGCCCCCCGCC<br>TGCTCATCCACTACACATCCACCCGCCAGACAGG<br>CATCCCGGCTCGATTCTCTGGTTCTGGCAGCGGT<br>CGTGATTACACCCTTACTATTTCTTCCCTGGAGC<br>CAGAGGACTTTGCGGTGTACTACTGCCTGCAGTA<br>TGACAACCTGCTGACCTTCGGCGGAGGCACCAAG<br>CTGGAGATCAAG | SEQ ID NO: 18 |

[Example 3]
Confirmation of Specificity of Selected Antibody to CD22

In the present invention, flow cytometry was performed to confirm the specificity of the 2G1 antibody (mouse) of Example 1 and the humanized 2G1(V4) and 2G1(V12) antibodies to CD22.

First, after $1 \times 10^6$ non-cell lymphoma U2932 (B-cell lymphoma U2932 cell) cells expressing CD22 were reacted with 1 μg of the 2G1 antibody for 30 minutes, the surface was stained with a secondary antibody, and then measured by a flow cytometer.

A PE-conjugated anti-CD22 antibody (Biolegend Inc., cat #302506, USA) was used as a positive control, and a PE-conjugated goat anti-mouse IgG (Biolegend Inc., cat #405307, USA) was used as the secondary antibody.

As a result, as illustrated in FIG. 1, it was confirmed that all of the 2G1 antibody and humanized 2G1(V4) and 2G1 (V12) antibodies specifically bound to cells expressing CD22.

[Example 4]
Construction of Chimeric Antigen Receptor (CD22-CAR) Expression Vector Targeting CD22

In the present invention, a lentiviral vector (CD22-CAR lentivirus) expressing the chimeric antigen receptor (CAR) targeting CD22 was constructed using the humanized 2G1 (V4) and 2G1(V12) antibodies prepared in Example 2.

As illustrated in the schematic view of FIG. 3,
CAR DNA including: an EF1α promoter (SEQ ID NO: 29);
a polynucleotide (SEQ ID NO: 30) encoding a signal peptide;
a polynucleotide (2G1-V4 represented by SEQ ID NO: 26 or 2G1-V12 represented by SEQ ID NO: 28) encoding a CD22-binding domain;
a polynucleotide (SEQ ID NO: 31) encoding a CD8 hinge region;
a polynucleotide (SEQ ID NO: 32) encoding a transmembrane domain;
a polynucleotide (SEQ ID NO: 33) encoding 4-1BB (costimulatory domain);
a polynucleotide (SEQ ID NO: 34) encoding CD3 (intracellular signal transduction domain); and
a polynucleotide (SEQ ID NO: 35) encoding WPRE was synthesized in vitro and inserted into a $3^{rd}$ generation lentiviral vector.

The lentiviral vector was co-infected into HEK293FT cells with three vectors of pMDLg/pRRE (Addgene, cat ##12251) pMD2.G (Addgene, cat ##12259), and pRSV-Rev (Addgene, cat ##12253), and then a CD22-CAR lentiviral vector was produced. For co-infection, the three vectors and HEK293FT cells were cultured for 4 hours using a Lipofectamine 3000 transfection kit (Invitrogen, cat #L3000-015) and a medium of Opti-MEM+GlutaMAX (Gibco, cat #51985-034).

Figure 4:
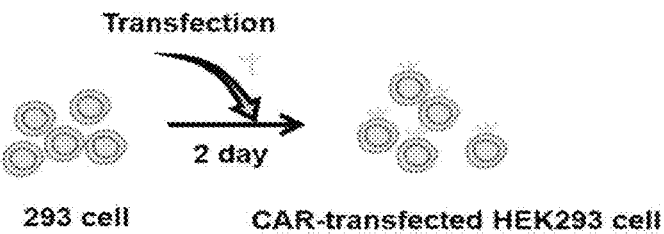
FIG. 4 is a schematic view illustrating (A) a method for transforming a HEK293 cell line with a CD22-CAR-expressing lentivirus and (B) a method for confirming the binding ability of the transformed HEK293 cells to a CD22 peptide.
Figure 4:
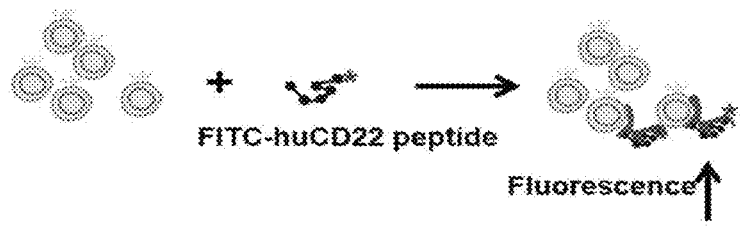

As a result of confirming whether a CAR specific for CD22 was expressed in HEK293FT transfected with the lentiviral vector (FIG. 4B), as illustrated in FIG. 5, it was confirmed that an anti-CD22 antibody was normally expressed.

[Example 5]
Preparation of CD22-CAR-T Cells

In the present invention, humanized anti-CD22 antibody (2G1(V4) and 2G1(V12))-based CD22-CAR-T cells were respectively prepared by transforming T cells with the CD22-CAR lentiviral vector prepared in Example 4.

Specifically, as in the schematic view illustrated in FIG. 7, peripheral blood mononuclear cells (PBMCs) were isolated from blood, and then T cells were activated using T cell activation beads (Miltenyl Biotec, cat #130-091-441). CD22-CAR-T cells were prepared by transducing the CD22-CAR lentivirus prepared in Example 4 into the activated T cells.

The ability of CD22-CAR-T cells to bind to the CD22 peptide was confirmed by a flow cytometry method. After the CD22-CAR-T cells (2G1-V4 and 2G1-V12) were classified into CD22-CAR-T cells in which CD3, CD4, or CD8 was activated using anti-CD3, anti-CD4, and anti-CD8 antibodies, respectively, and then reacted with an FITC-CD22 peptide, fluorescence intensity was measured using an FACS instrument.

As a result, as illustrated in FIG. 8, it was confirmed that all the CD22-CAR-T cells in which CD3, CD4 or CD8 was activated bound to the CD22 peptide.

[Example 6]

Confirmation of Apoptotic Effect of CD22-CAR-T Cells on CD22-Expressing Cells

In the present invention, the apoptotic effect of humanized anti-CD22 antibody (2G1(V4) and 2G1(V12))-based CD22-CAR-T cells on target cells was confirmed.

As the target cells, K562 cells (human erythroleukemic cell line) which do not express CD22 and U2932 cells (B cell lymphoma) and NALM6 cells (human B cell precursor leukemia) expressing CD22 were used, and cultured for 8 hours by being mixed with CD22-CAR-T cells so as to have a ratio of 1:4, 1:2, 1:1, 1:0.5 and 1:0.25, respectively, and then luminescence (CytoTox-Glo Cytotoxicity Assay, Promega, cat. NO G9291) was measured. The degree of cell apoptosis was calculated from the measured values using the following Equation 1.

% Cytotoxicity=[(Experimental−Effector Spontaneous−Target Spontaneous)/(Target Maximum−Target Spontaneous)]×100 [Equation 1]

Figure 10:
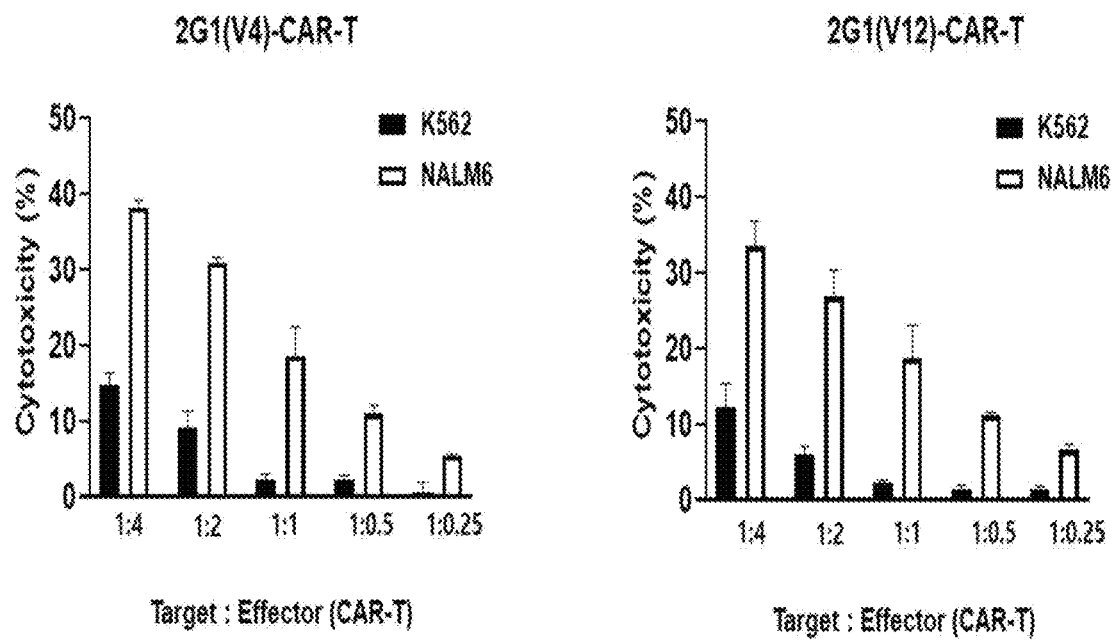
FIG. 10 illustrates the data confirming the apoptotic effects on NALM6 cells (CD22-expressing cells) and K562 cells (CD22-non-expressing cells) by 2G1(V4) and 2G1(V12)-based CD22-CAR-T cells, which are humanized anti-CD22 antibodies.

Experimental: Luminescence value derived from target cell and CAR-T cell composite culture medium Effector Spontaneous: Luminescence value derived from CAR-T cell-only medium Target Spontaneous: Luminescence value derived from target cell-only medium Target Maximum: Luminescence value derived from 100% lysis (using lysis reagent) of target cells As a result, as illustrated in FIGS. 9 and 10, it was confirmed that the humanized anti-CD22 antibody (2G1(V4) and 2G1(V12))-based CD22-CAR-T cells specifically killed U2932 cells and NALM6 cells expressing CD22.

In the present invention, through the experiment, it was confirmed that humanized anti-CD22 antibody (2G1(V4) and 2G1(V12))-based CD22-CAR-T cells specifically killed diffuse large B-cell lymphoma-derived U2932 cells and acute lymphoblastic leukemia-derived NALM6 cells.

That is, the humanized anti-CD22 antibody (2G1(V4) and 2G1(V12))-based chimeric antigen receptor of the present invention and CAR-T cells using the same may be usefully used as a composition for preventing or treating a disease related to B cells or CD22 expression.

[Example 7]

Construction of Bispecific Chimeric Antigen Receptor Expression Vector Targeting CD19/CD22

A lentiviral vector (CD19xCD22-CAR lentivirus) expressing a bispecific chimeric antigen receptor targeting CD19 and CD22 was prepared in the same manner as in Example 4.

As illustrated in the schematic view of FIG. 11,

CAR DNA including: an EF1α promoter (SEQ ID NO: 29);

a polynucleotide (SEQ ID NO: 30) encoding a signal peptide;

a polynucleotide encoding a CD19/CD22-binding domain;

a polynucleotide (SEQ ID NO: 31) encoding a CD8 hinge region;

a polynucleotide (SEQ ID NO: 32) encoding a transmembrane domain;

a polynucleotide (SEQ ID NO: 33) encoding 4-1BB (costimulatory domain);

a polynucleotide (SEQ ID NO: 34) encoding CD3ζ (intracellular signal transduction domain); and a polynucleotide (SEQ ID NO: 35) encoding WPRE was synthesized in vitro and inserted into a $3^{rd}$ generation lentiviral vector.

In the present invention, a known anti-CD19 antibody (FMC63) was used as a CD19-binding domain, and the 2G1 antibody, 2G1(V4) antibody and 2G1(V12) antibody of the present invention were used as a CD22-binding domain.

The CD19xCD22-binding domain may be linked in the order of a light chain variable region (CD19VL) of an antibody specifically binding to CD19—a heavy chain variable region (CD22VH) of an antibody specifically binding to CD22—a light chain variable region (CD22VL) of an antibody specifically binding to CD22—a heavy chain variable region (CD19VH) of an antibody specifically binding to CD19 (LoopCAR), and the sequence information on the polynucleotides encoding these is as follows:

CD19x 2G1: CD19VL represented by a base sequence of SEQ ID NO: 50—a linker (linker 1 in FIG. 11) represented by a base sequence of SEQ ID NO: 52—CD22VH represented by a base sequence of SEQ ID NO: 9—a linker (linker 6 in FIG. 11) represented by a base sequence of SEQ ID NO: 55—CD22VL represented by a base sequence of SEQ ID NO: 10—a linker (linker 1 in FIG. 1) represented by a base sequence of SEQ ID NO: 53—CD19VH represented by a base sequence of SEQ ID NO: 49;

CD19x2G1(V4): CD19VL represented by a base sequence of SEQ ID NO: 50—a linker (linker 1 in FIG. 11) represented by a base sequence of SEQ ID NO: 52—CD22VH represented by a base sequence of SEQ ID NO: 13—a linker (linker 6 in FIG. 11) represented by a base sequence of SEQ ID NO: 55—CD22VL represented by a base sequence of SEQ ID NO: 14—a linker (linker 1 in FIG. 1) represented by a base sequence of SEQ ID NO: 53—CD19VH represented by a base sequence of SEQ ID NO: 49;

CD19x2G1(V12): CD19VL represented by a base sequence of SEQ ID NO: 50—a linker (linker 1 in FIG. 11) represented by a base sequence of SEQ ID NO: 52—CD22VH represented by a base sequence of SEQ ID NO: 17—a linker (linker 6 in FIG. 11) represented by a base sequence of SEQ ID NO: 55—CD22VL represented by a base sequence of SEQ ID NO: 18—a linker (linker 1 in FIG. 1) represented by a base sequence of SEQ ID NO: 53—CD19VH represented by a base sequence of SEQ ID NO: 49.

The lentiviral vector was co-infected into HEK293FT cells with three vectors of pMDLg/pRRE (Addgene, cat ##12251) pMD2.G (Addgene, cat ##12259), and pRSV-Rev (Addgene, cat ##12253), and then a CD19/CD22-CAR lentiviral vector was produced. For co-infection, the three vectors and HEK293FT cells were cultured for 4 hours using a Lipofectamine 3000 transfection kit (Invitrogen, cat #L3000-015) and a medium of Opti-MEM+GlutaMAX (Gibco, cat #51985-034).

As a result of confirming whether a CAR specific for CD19xCD22 was expressed in HEK293FT transfected with the lentiviral vector, as illustrated in FIGS. 13 and 14, it was confirmed that an anti-CD19/anti-CD22 antibody was normally expressed.

[Example 8]

Preparation of CD19xCD22-CAR-T Cells

In the present invention, C19x2G1, C19x2G1(V4) and CD19x2G1(V12), which are CD19xCD22-CAR-T cells, were respectively prepared by transforming T cells with the CD19xCD22-CAR lentiviral vector prepared in Example 7 in the same manner as in Example 5.

The ability of CD19xCD22-CAR-T cells to bind to the CD22 peptide was confirmed by a flow cytometry method. After the CD19xCD22-CAR-T cells (CD19x 2G1, CD19x 2G1(V4) and CD19 x2G1(V12)) were classified into CD19xCD22-CAR-T cells in which CD3, CD4, or CD8 was activated using anti-CD3, anti-CD4, and anti-CD8 antibodies, respectively, and then reacted with a PE-CD19 peptide and an FITC-CD22 peptide, fluorescence intensity was measured using a flow cytometer.

As a result, as illustrated in FIG. 16, it was confirmed that all the CD19xCD22-CAR-T cells in which CD3, CD4 or CD8 was activated bound to the CD19 peptide and the CD22 peptide.

[Example 9]
Confirmation of Activation of CD19xCD22-CAR-T Cells in CD22-Expressing Cells In the present invention, in order to confirm whether the CD19xCD22-CAR-T cells prepared in Example 8 were specifically activated by CD22-expressing cells, the expression level of IFNγ by CD19xCD22-CAR-T cells was confirmed in the presence of target cells.

As the target cells, K562 cells (ATCC, cat #CCL-243) which do not express CD19 and CD22 and NALM6 cells (human B cell precursor leukemia) expressing CD19 and CD22 were used, and CD19/CD22-CAR-T cells and the target cells were reacted at a ratio of 2:1, 1:1, 0.5:1, and 0.25:1 for a certain period of time, and then stained with a surface & intra antibody, and measured by a flow cytometer (INF-r, CD4, and CD8 staining).

As a result, as illustrated in FIGS. 17A to 17C, it was confirmed that T cells were not activated in K562 cells that do not express CD19 and CD22, whereas T cells were activated in the presence of NALM6 cells expressing CD19 and CD22, thereby increasing the expression of IFNγ.

[Example 10]
Confirmation of Apoptotic Effect of CD19xCD22 Cells on CD22 or CD19 Expression Cells In the present invention, the apoptotic effect of humanized anti-CD22 antibody (2G1(V4) and 2G1(V12))-based CD19xCD22-CAR-T cells on target cells was confirmed.

As the target cells, K562 cells (human erythroleukemic cell line) which do not express CD22 and NALM6 cells (human B cell precursor leukemia) expressing CD19 and CD22 were used, and cultured for 8 hours by being mixed with CD19xCD22-CAR-T cells so as to have a ratio of 1:4, 1:2, 1:1, 1:0.5 and 1:0.25, respectively, and then luminescence (CytoTox-Glo Cytotoxicity Assay, Promega, cat #G9291) was measured. The degree of cell apoptosis was calculated from the measured values using Equation 1 in Example 6.

Figure 18A:
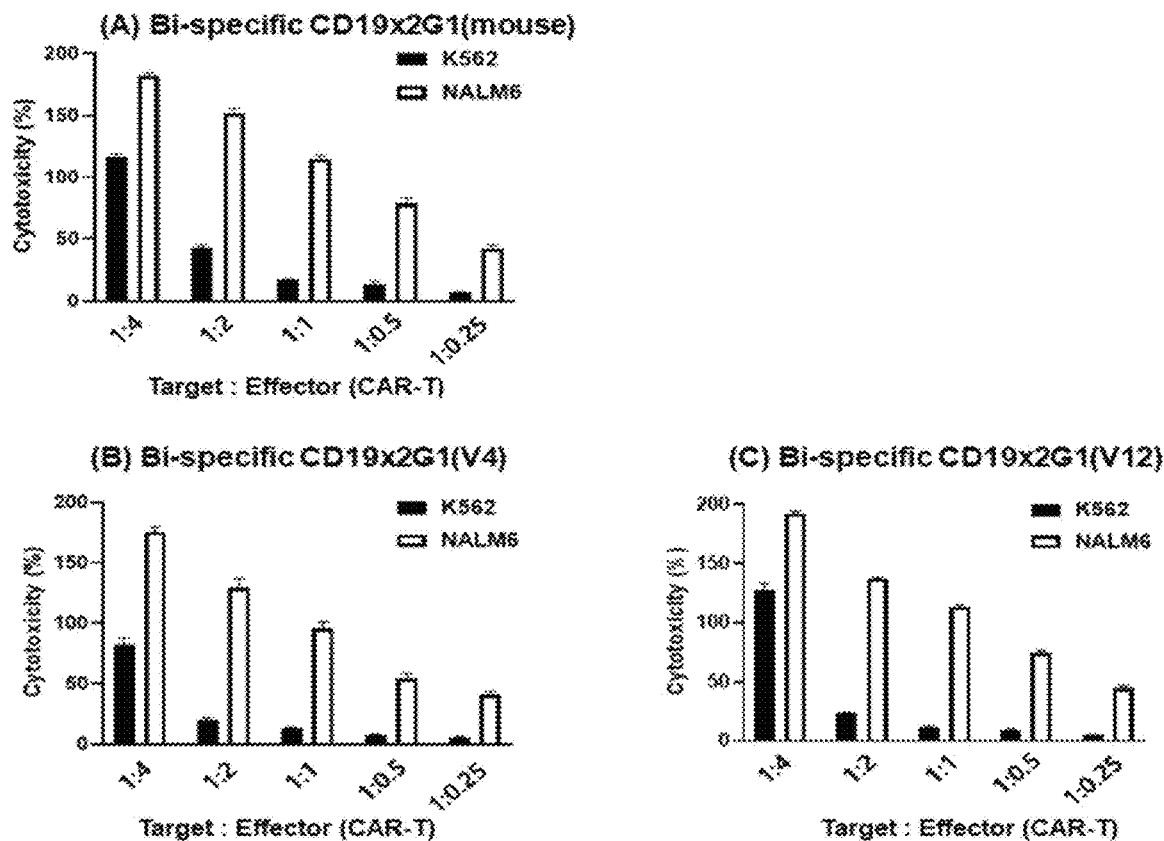
FIGS. 18a-18b illustrate the data confirming the apoptotic effects on (A) NALM6 cells (CD19 and CD22-expressing cells), (B) K562 cells (CD19 and CD22-non-expressing cells), K562/CD19+ cells (CD19-expressing cells), K562/CD22+ cells (CD22-expressing cells), and K562/CD19+/CD22+ cells (CD19 and CD22-expressing cells) by CD19xCD22-CAR-T cells.

As a result, as illustrated in FIG. 18A, it was confirmed that mouse-derived 2G1-based CD19x2G1 CAR-T, humanized antibody-based CD19x2G1(V4) CAR-T of 2G1 and other humanized antibody-based CD19x2G1(V12) CAR-T cells of 2G1 specifically killed NALM6 cells expressing CD22 and CD19.

Figure 18B:
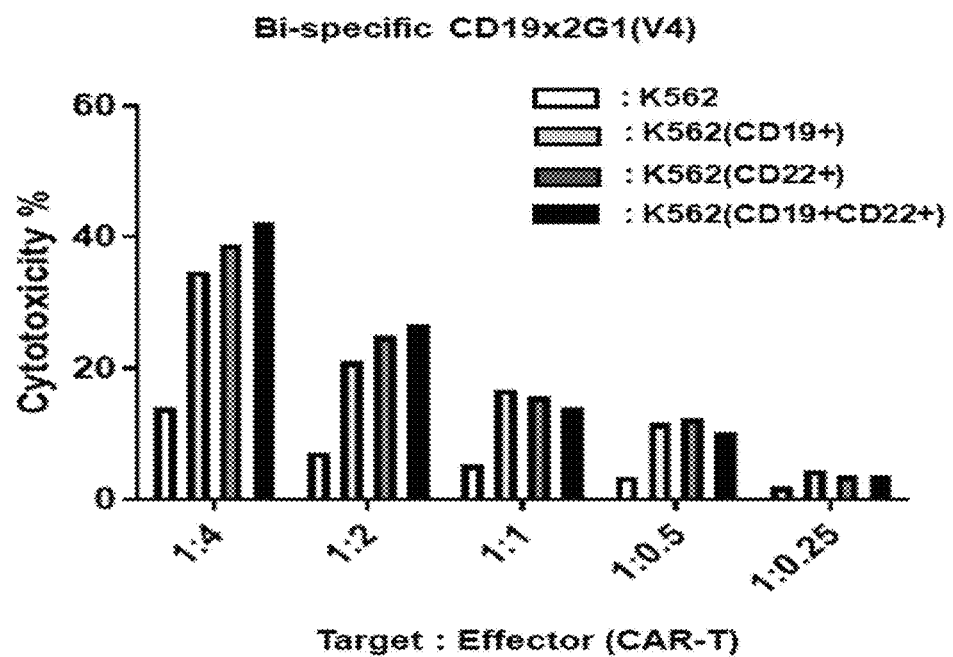

In the present invention, K562 cells (ATCC, cat #CCL-243) which do not express CD19 and CD22 and three cells K562/CD19+, K562/CD22+, and K562/CD19+/CD22+ expressing CD19 or CD22 or CD19xCD22 were constructed, and the apoptotic effect of humanized antibody-based CD19x2G1(V4) CAR-T cells on the target cells was confirmed. As a result, as illustrated in FIG. 18B, it was confirmed that CD19x2G1(V4) CAR-T cells specifically killed cells expressing CD22 or CD19 or CD19/CD22.

[Example 11]
Confirmation of Antitumor Effects of CD19/CD22-CAR-T Cells in Animal Model In the present invention, the antitumor effects of CD19 x CD22-CAR-T cells were confirmed using a mouse model in which tumor cells were xenografted.

After $1\times10^6$ NALM6/Luc cells were injected into 9-week-old NOD/SCID mice by intravenous injection, $0.5\times10^6$ (low), $1\times10^6$ (medium), and $5\times10^6$ (high) CD19xCD22-CAR-T cells were injected by intravenous injection on day 5, and $1.25\times10^7$ Palivizumab CAR-T cells as a positive control were injected. After cell injection, the antitumor effects by suppressing the proliferation of the NALM6/Luc cells were observed by capturing the luminescence expressed in the NAML6/Luc cells ex vivo by IVIS SpectrumCT on days 3, 8, 15, 22, and 29.

Figure 19A:
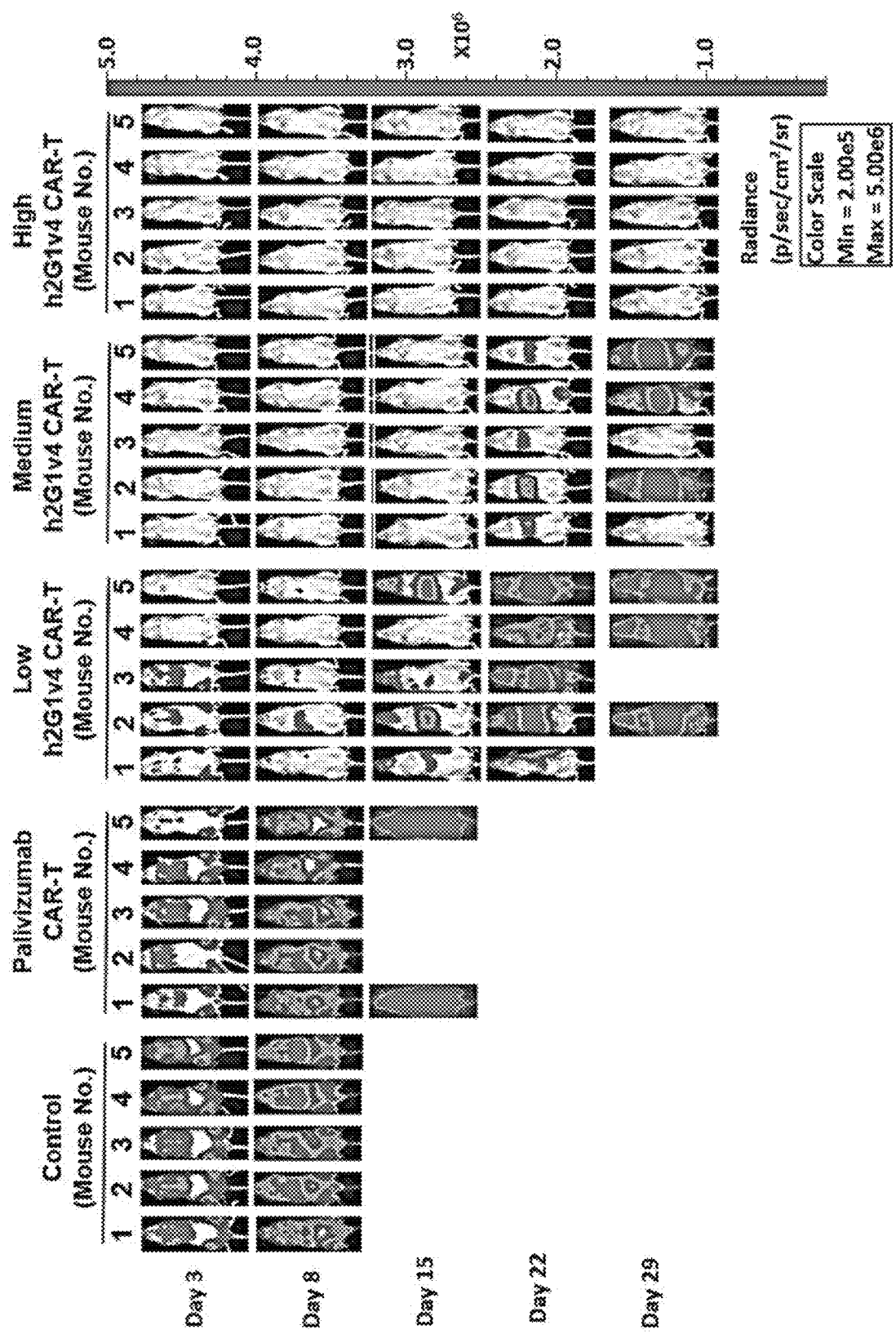
FIGS. 19a-19b illustrate (A) images of luminescence expressed in NALM6/Luc cells injected into mice taken by IVIS Spectrum CT, and (B) data showing an antitumor effect by a viability curve of mice in experiments performed in (A), in order to confirm the anti-tumor effects of CD19xCD22(V4)-CAR-T cells.

As a result, as illustrated in FIG. 19A, it was confirmed that the antitumor effects of the CD19xCD22-CAR-T cells of the present invention were excellent compared to those of palivizumab-CAR-T cells derived from a scFv of the antibody palivizumab binding to the SV40 virus used as a positive control and an animal group into which CAR-T was not injected, and it was confirmed that when CD19xCD22-CAR-T cells were treated at $5\times10^6$ or more, most of the tumor cells were killed, and thus no tumor cells expressing luminescence were observed until day 29 after CAR-T injection.

Figure 19B:
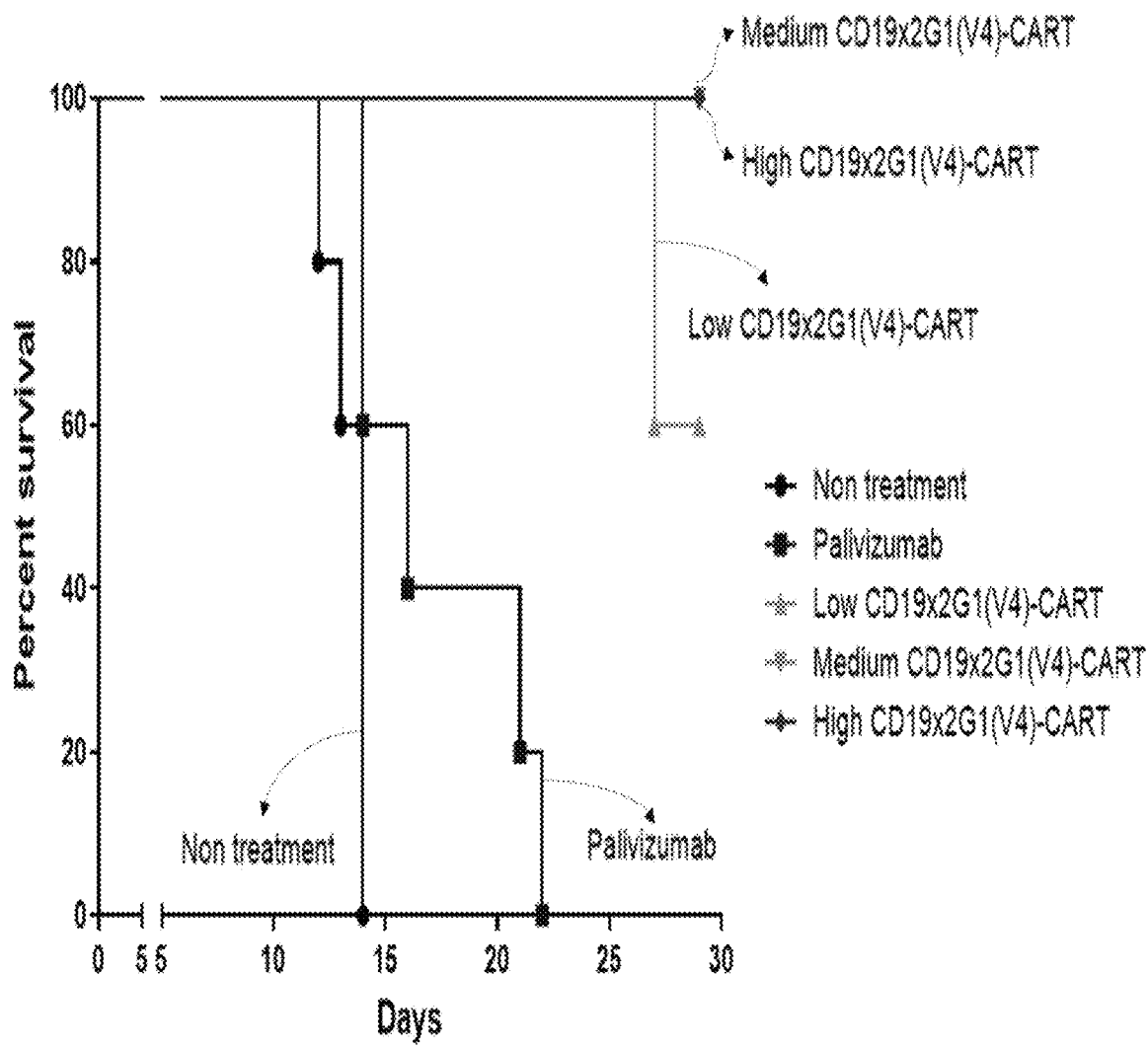

As a result of showing these results as the survival rate curve in FIG. 19B, it was confirmed that all the mice injected with CD19xCD22-CAR-T at $1\times10^6$ (medium) and $5\times10^6$ (high) survived until day 29.

The invention claimed is:

1. A humanized antibody or a fragment thereof that specifically binds to CD22, wherein said antibody or fragment thereof comprises: a heavy chain variable region represented by the amino acid sequence of SEQ ID NO: 11 and a light chain variable region represented by the amino acid sequence of SEQ ID NO: 12; or a heavy chain variable region represented by the amino acid sequence of SEQ ID NO: 15 and a light chain variable region represented by the amino acid sequence of SEQ ID NO: 16.

2. A polynucleotide encoding the humanized antibody or fragment thereof of claim 1.

3. A vector comprising a polynucleotide encoding the humanized antibody or fragment thereof of claim 1.

4. A recombinant cell comprising the vector of claim 3.

5. A pharmaceutical composition comprising the humanized antibody or fragment thereof of claim 1 and a pharmaceutically acceptable carrier.

6. A method of treating a subject suffering from a disease mediated by B cells, comprising administering the pharmaceutical composition of claim 5.

7. The method of claim 6, wherein the disease mediated by B cells is selected from the group consisting of tumor, lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma (SLL), leukemia, hairy cell leukemia (HCL), acute lymphocytic leukemia (ALL), Burkitt's lymphoma, and mantle cell lymphoma.

8. A chimeric antigen receptor targeting CD22, comprising: a CD22-binding domain;
a transmembrane domain;
a costimulatory domain;
and an intracellular signal transduction domain,
wherein the CD22-binding domain is a humanized antibody or a fragment thereof that specifically binds to CD22, wherein said antibody or fragment thereof comprises a heavy chain variable region represented by the amino acid sequence of SEQ ID NO: 11 and a light chain variable region represented by the amino acid sequence of SEQ ID NO: 12; or a heavy chain variable region represented by the amino acid sequence of SEQ ID NO: 15 and a light chain variable region represented by the amino acid sequence of SEQ ID NO: 16.

9. The chimeric antigen receptor of claim 8, wherein the transmembrane domain is a protein selected from the group consisting of CD8α, CD4, CD28, CD137, CD80, CD86, CD152 and PD1,
the costimulatory domain is a protein selected from the group consisting of CD28, 4-1BB, OX-40 and ICOS, and
the intracellular signal transduction domain is CD3ζ.

10. A polynucleotide encoding the chimeric antigen receptor of claim 9.

11. A vector or an immune effector cell comprising a polynucleotide encoding the chimeric antigen receptor of claim 9.

12. An immune effector cell comprising a vector comprising a polynucleotide encoding the chimeric antigen receptor of claim 9.

13. A pharmaceutical composition comprising the immune effector cell of claim 12 and a pharmaceutically acceptable carrier.

14. A method of treating a subject suffering from a disease mediated by B cells comprising administering the pharmaceutical composition of claim 13 to the subject.

15. The method of claim 14, wherein the disease mediated by B cells is selected from the group consisting of tumor, lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma (SLL), leukemia, hairy cell leukemia (HCL), acute lymphocytic leukemia (ALL), Burkitt's lymphoma, and mantle cell lymphoma.

16. The chimeric antigen receptor of claim 8, further comprising a hinge region between a C-terminus of the binding domain and an N-terminus of the transmembrane domain.

17. A vector or an immune effector cell comprising a polynucleotide encoding the chimeric antigen receptor of claim 16.

18. A polynucleotide encoding the chimeric antigen receptor of claim 8.

19. A vector or an immune effector cell comprising a polynucleotide encoding the chimeric antigen receptor of claim 8.

20. An immune effector cell comprising a vector comprising a polynucleotide encoding the chimeric antigen receptor of claim 8.

* * * * *

SEQUENCE LISTING

```
Sequence total quantity: 55
SEQ ID NO: 1           moltype = AA  length = 9
FEATURE                Location/Qualifiers
REGION                 1..9
                       note = 2G1_VH_CDR1
source                 1..9
                       mol_type = protein
                       organism = synthetic construct
SEQUENCE: 1
GFSLTSYDI                                                                 9

SEQ ID NO: 2           moltype = AA  length = 7
FEATURE                Location/Qualifiers
REGION                 1..7
                       note = 2G1_VH_CDR2
source                 1..7
                       mol_type = protein
```

```
                        organism = synthetic construct
SEQUENCE: 2
IWTGGGT                                                                      7

SEQ ID NO: 3            moltype = AA    length = 12
FEATURE                 Location/Qualifiers
REGION                  1..12
                        note = 2G1_VH_CDR3
source                  1..12
                        mol_type = protein
                        organism = synthetic construct
SEQUENCE: 3
VPHYYGYAMD YW                                                               12

SEQ ID NO: 4            moltype = AA    length = 6
FEATURE                 Location/Qualifiers
REGION                  1..6
                        note = 2G1_VL_CDR1
source                  1..6
                        mol_type = protein
                        organism = synthetic construct
SEQUENCE: 4
QDINKY                                                                       6

SEQ ID NO: 5            moltype =    length =
SEQUENCE: 5
000

SEQ ID NO: 6            moltype = AA    length = 8
FEATURE                 Location/Qualifiers
REGION                  1..8
                        note = 2G1_VL_CDR3
source                  1..8
                        mol_type = protein
                        organism = synthetic construct
SEQUENCE: 6
LQYDNLLT                                                                     8

SEQ ID NO: 7            moltype = AA    length = 117
FEATURE                 Location/Qualifiers
REGION                  1..117
                        note = 2G1_VH
source                  1..117
                        mol_type = protein
                        organism = synthetic construct
SEQUENCE: 7
EVQLQESGPG LVAPSQSLSI TCTVSGFSLT SYDISWIRQP PGKGLEWLGV IWTGGGTNYN            60
SAFMSRLSIS KDNSKSQVFL KMNSLQTDDT AIYYCVPHYY GYAMDYWGQG TSVTVSS              117

SEQ ID NO: 8            moltype = AA    length = 106
FEATURE                 Location/Qualifiers
REGION                  1..106
                        note = 2G1_VL
source                  1..106
                        mol_type = protein
                        organism = synthetic construct
SEQUENCE: 8
DIVLTQSPSS LSASLGGKVT ITCKASQDIN KYIAWYQHKP GKGPRLLIHY TSTLQPGIPS            60
RFSGSGSGRD YSFSISNLEP EDIATYYCLQ YDNLLTFGAG TKLELK                          106

SEQ ID NO: 9            moltype = DNA    length = 351
FEATURE                 Location/Qualifiers
misc_feature            1..351
                        note = 2G1_VH
source                  1..351
                        mol_type = other DNA
                        organism = synthetic construct
SEQUENCE: 9
gaggtgcagc tgcaggagtc aggacctggc ctggtggcgc cctcacagag cctgtccatt            60
acctgcactg tctctgggtt ctcattaacc agctatgata taagctggat tcgccagcca          120
ccaggaaagg gtctggagtg gcttggagta atatgactg gtggaggcac aaattataat           180
tcagctttca gtccagact gagcatcagc aaggacaact ccaagagcca agttttctta           240
aaaatgaaca gtctgcaaac tgatgacaca gccatatatt actgtgtccc tcattactac          300
ggctatgcta tggactactg gggtcaagga acctcagtca ccgtctcctc a                   351

SEQ ID NO: 10           moltype = DNA    length = 318
FEATURE                 Location/Qualifiers
misc_feature            1..318
                        note = 2G1_VL
```

| | | |
|---|---|---|
| source | 1..318 | |
| | mol_type = other DNA | |
| | organism = synthetic construct | |

SEQUENCE: 10
```
gatattgtgc tgacccagtc tccatcctca ctgtctgcat ctctgggagg caaagtcacc   60
atcacttgca aggcaagcca agacattaac aagtatatag cttggtacca acacaagcct  120
ggaaaaggtc ctaggctgct catacattac acatctacat tacagccagg catcccatca  180
aggttcagtg gaagtgggtc tgggagagat tattccttca gcatcagcaa cctggagcct  240
gaagatattg caacttatta ttgtctacag tatgataatc tgctcacgtt cggtgctggg  300
accaagctgg agctgaaa                                                318
```

| | | |
|---|---|---|
| SEQ ID NO: 11 | moltype = AA length = 117 | |
| FEATURE | Location/Qualifiers | |
| REGION | 1..117 | |
| | note = 2G1-V4_VH | |
| source | 1..117 | |
| | mol_type = protein | |
| | organism = synthetic construct | |

SEQUENCE: 11
```
EVQLQESGPG LVKPSQTLSL TCTVSGFSLT SYDISWIRQP PGKGLEWLGV IWTGGGTNYN   60
SALKSRVTIS KDNSKSQVSL KLSSVTAADT AVYYCVPHYY GYAMDYWGQG TTVTVSS     117
```

| | | |
|---|---|---|
| SEQ ID NO: 12 | moltype = AA length = 106 | |
| FEATURE | Location/Qualifiers | |
| REGION | 1..106 | |
| | note = 2G1-V4_VL | |
| source | 1..106 | |
| | mol_type = protein | |
| | organism = synthetic construct | |

SEQUENCE: 12
```
EIVLTQSPAT LSLSPGERAT LSCRASQDIN KYIAWYQQKP GQAPRLLIHY TSTRQTGIPA   60
RFSGSGSGRD YTLTISSLEP EDFAVYYCLQ YDNLLTFGGG TKLEIK                 106
```

| | | |
|---|---|---|
| SEQ ID NO: 13 | moltype = DNA length = 351 | |
| FEATURE | Location/Qualifiers | |
| misc_feature | 1..351 | |
| | note = 2G1-V4_VH | |
| source | 1..351 | |
| | mol_type = other DNA | |
| | organism = synthetic construct | |

SEQUENCE: 13
```
gaggtgcagc tgcaggagag cggccccggc ctggtgaagc cgagccagac tctttctctg   60
acctgcaccg tgtccggctt ctctcttacg agctacgaca tctcgtggat ccggcagccg  120
cctgggaaag gcttagagtg gctaggggtg atttggaccg gcggggtac caactacaac  180
tccgcgctca atcccgcgt cactatttct aaggacaatt ccaagagcca ggtctcgctg  240
aagtctcgt ccgtgaccgc cgcggacacc gcagtttatt actgcgtgcc tcattactac  300
ggctacgcca tggattattg gggccagggc accacagtaa cagtcagctc c           351
```

| | | |
|---|---|---|
| SEQ ID NO: 14 | moltype = DNA length = 318 | |
| FEATURE | Location/Qualifiers | |
| misc_feature | 1..318 | |
| | note = 2G1-V4_VL | |
| source | 1..318 | |
| | mol_type = other DNA | |
| | organism = synthetic construct | |

SEQUENCE: 14
```
gagatcgtgc tgactcagag cccggccacc cttagcctga gtccaggcga gcgcgctacg   60
ttgtcatgcc gagcttccca ggacattaac aagtacatcg cgtggtacca gcagaagccc  120
ggacaggccc cccgcctgct catccactac acctccaccc gccagactgg catccctgcc  180
aggttttcag gctccggttc tggccgtgac tacacccctga ccatctctag tttggagccc  240
gaagatttcg ccgtgtacta ctgtctgcaa tatgacaacc tgctgacctt cggaggggt   300
accaagctgg agatcaag                                                318
```

| | | |
|---|---|---|
| SEQ ID NO: 15 | moltype = AA length = 117 | |
| FEATURE | Location/Qualifiers | |
| REGION | 1..117 | |
| | note = 2G1-V12_VH | |
| source | 1..117 | |
| | mol_type = protein | |
| | organism = synthetic construct | |

SEQUENCE: 15
```
EVQLKESGPV LVKPTETLTL TCTVSGFSLT SYDISWIRQP PGKALEWLGV IWTGGGTNYN   60
SALKSRLTIS KDNSKSQVVL TMTNMDPVDT ATYYCVPHYY GYAMDYWGQG TTVTVSS     117
```

| | | |
|---|---|---|
| SEQ ID NO: 16 | moltype = AA length = 106 | |
| FEATURE | Location/Qualifiers | |
| REGION | 1..106 | |
| | note = 2G1-V12_VL | |
| source | 1..106 | |

```
                                 mol_type = protein
                                 organism = synthetic construct
SEQUENCE: 16
EIVLTQSPAT  LSLSPGERAT  LSCRASQDIN  KYIAWYQQKP  GQAPRLLIHY  TSTRQTGIPA    60
RFSGSGSGRD  YTLTISSLEP  EDFAVYYCLQ  YDNLLTFGGG  TKLEIK                   106

SEQ ID NO: 17              moltype = DNA   length = 351
FEATURE                    Location/Qualifiers
misc_feature               1..351
                           note = 2G1-V12_VH
source                     1..351
                           mol_type = other DNA
                           organism = synthetic construct
SEQUENCE: 17
gaggtgcagc tgaaggagag cgggccggtg ctggtgaagc ctaccgagac tctgaccctg    60
acctgcactg tttccggctt ctctctgacg agctacgaca tcagttggat ccgccagcca   120
cccggcaaag cgttggaatg gctcggggta atttggaccg gtggcgggac caactacaac   180
agcgcgctca aatcgcggct aaccatctca aaggacaact ccaagtccca agtggtgtta   240
actatgacaa atatggatcc ggtcgacacc gctaccatt actgcgtgcc tcattactac   300
ggctacgcca tggattattg gggccagggc acgaccgtga ccgtctccag t            351

SEQ ID NO: 18              moltype = DNA   length = 318
FEATURE                    Location/Qualifiers
misc_feature               1..318
                           note = 2G1-V12_VL
source                     1..318
                           mol_type = other DNA
                           organism = synthetic construct
SEQUENCE: 18
gagatcgtgt tgacccagag ccctgccacg ctgagcctgt cccccgggga gcgcgccact    60
ctttcgtgta gggcttccca ggacattaac aagtacatcg catggtacca gcagaagccc   120
ggacaggccc ccgcctgct catccactac acatccaccc gccagacagg catcccggct   180
cgattctctg gttctggcag cggtcgtgat tacaccctta ctatttcttc cctgagcca   240
gaggactttg cggtgtacta ctgcctgcag tatgacaacc tgctgacctt cggcggaggc   300
accaagctgg agatcaag                                                  318

SEQ ID NO: 19              moltype = AA   length = 15
FEATURE                    Location/Qualifiers
REGION                     1..15
                           note = scfv linker
source                     1..15
                           mol_type = protein
                           organism = synthetic construct
SEQUENCE: 19
GGGGSGGGGS GGGGS                                                       15

SEQ ID NO: 20              moltype = DNA   length = 45
FEATURE                    Location/Qualifiers
misc_feature               1..45
                           note = scfv linker
source                     1..45
                           mol_type = other DNA
                           organism = synthetic construct
SEQUENCE: 20
ggcggaggcg gcagcggcgg aggcggctct ggcggcggcg ggagc                     45

SEQ ID NO: 21              moltype = DNA   length = 45
FEATURE                    Location/Qualifiers
misc_feature               1..45
                           note = scfv linker
source                     1..45
                           mol_type = other DNA
                           organism = synthetic construct
SEQUENCE: 21
ggggcggcg gatctggtgg tggaggctcc ggcggtggcg gttcc                      45

SEQ ID NO: 22              moltype = DNA   length = 45
FEATURE                    Location/Qualifiers
misc_feature               1..45
                           note = scfv linker
source                     1..45
                           mol_type = other DNA
                           organism = synthetic construct
SEQUENCE: 22
ggcggcggtg gctccggtgg aggcggatct ggcggtggcg ggtcg                     45

SEQ ID NO: 23              moltype = AA   length = 238
FEATURE                    Location/Qualifiers
REGION                     1..238
```

```
                        note = 2G1 scfv
source                  1..238
                        mol_type = protein
                        organism = synthetic construct
SEQUENCE: 23
DIVLTQSPSS LSASLGGKVT ITCKASQDIN KYIAWYQHKP GKGPRLLIHY TSTLQPGIPS    60
RFSGSGSGRD YSFSISNLEP EDIATYYCLQ YDNLLTFGAG TKLELKGGGG SGGGGSGGGG   120
SEVQLQESGP GLVAPSQSLS ITCTVSGFSL TSYDISWIRQ PPGKGLEWLG VIWTGGGTNY   180
NSAFMSRLSI SKDNSKSQVF LKMNSLQTDD TAIYYCVPHY YGYAMDYWGQ GTSVTVSS    238

SEQ ID NO: 24           moltype = DNA   length = 714
FEATURE                 Location/Qualifiers
misc_feature            1..714
                        note = 2G1 scfv
source                  1..714
                        mol_type = other DNA
                        organism = synthetic construct
SEQUENCE: 24
gatatcgtgc tgacccagag ccctttctagc ctgagcgcct ctctgggcgg caaggtgacc    60
atcacctgca aggccagcca ggacatcaac aagtacatcg cctggtacca gcacaagcct   120
ggaaaaggcc ctagactgct gatccactac accagcacac tccagcctgg catccccagc   180
agattcagcg gatctggaag cggcagagat tacagcttca gcatttctaa tctgaaacct   240
gaggacatcg ctacatacta ttgtctgcag tacgacaacc tgctgacctt cggcgctggc   300
accaagctgg agctgaaagg cggaggcggc agcggcggag cggctctgg cggcggcggg   360
agcgaggtgc agctgcagga gagcggcccc ggactggtcg ccccaagcca atctctgtcc   420
atcacatgca ccgtgtccgg ctttagcctg acatcatatg atatcagctg gatccggcag   480
ccacctggca agggcctgga atggctgggc gttatctgat ccggcggagg cacaaactac   540
aactccgcct tcatgagccg gctgagcatc tctaaggaca tagcaagtc ccaggtgttc   600
ctgaagatga acagcctgca aacagacgac accgccatct actactgcgt gccccactac   660
tacggctacg ccatggacta ctggggccag ggcaccagcg tgaccgtgtc cagc        714

SEQ ID NO: 25           moltype = AA    length = 238
FEATURE                 Location/Qualifiers
REGION                  1..238
                        note = 2G1-V4 scfv
source                  1..238
                        mol_type = protein
                        organism = synthetic construct
SEQUENCE: 25
EIVLTQSPAT LSLSPGERAT LSCRASQDIN KYIAWYQQKP GQAPRLLIHY TSTRQTGIPA    60
RFSGSGSGRD YTLTISSLEP EDFAVYYCLQ YDNLLTFGGG TKLEIKGGGG SGGGGSGGGG   120
SEVQLQESGP GLVKPSQTLS LTCTVSGFSL TSYDISWIRQ PPGKGLEWLG VIWTGGGTNY   180
NSALKSRVTI SKDNSKSQVS LKLSSVTAAD TAVYYCVPHY YGYAMDYWGQ GTTVTVSS    238

SEQ ID NO: 26           moltype = DNA   length = 714
FEATURE                 Location/Qualifiers
misc_feature            1..714
                        note = 2G1-V4 scfv
source                  1..714
                        mol_type = other DNA
                        organism = synthetic construct
SEQUENCE: 26
gagatcgtgc tgactcagag cccggccacc cttagcctga gtccaggcga gcgcgctacg    60
ttgtcatgcc gagcttccca ggacattaac aagtacatcg cgtggtacca gcagaagccc   120
ggacaggccc cccgcctgct catccactac acctccaccg gccagactgg catccctag   180
aggttttcag gctccggttc tggccgtgac tacaccctga ccatctctag tttggagccc   240
gaagatttcg ccgtgtacta ctgtctgcaa atgacaacc tgctgacctt cggagggggt   300
accaagctgg agatcaaggg gggcggcgga tctggtggtg gaggctccgg cggtggcggt   360
tccgaggtgc agctgcagga gagcggcccc ggccttgtga agccagcca gactctttct   420
ctgacctgca ccgtgtccgg cttctctctt acgagctacg acatccgtg gatccggcag   480
ccgcctggga aaggcttaga gtggctaggg gtgatttgga ccggcggggg taccaactac   540
aactccgcgc tcaaatcccg cgtcactatt tctaaggaca attccaagag ccaggtctcg   600
ctgaagctct cgtccgtgac cgccgcggac accgcagttt attactgcgt gcctcattac   660
tacggctacg ccatggatta ttggggccag ggcaccacag taacagtcag ctcc        714

SEQ ID NO: 27           moltype = AA    length = 238
FEATURE                 Location/Qualifiers
REGION                  1..238
                        note = 2G1-V12 scfv
source                  1..238
                        mol_type = protein
                        organism = synthetic construct
SEQUENCE: 27
EIVLTQSPAT LSLSPGERAT LSCRASQDIN KYIAWYQQKP GQAPRLLIHY TSTRQTGIPA    60
RFSGSGSGRD YTLTISSLEP EDFAVYYCLQ YDNLLTFGGG TKLEIKGGGG SGGGGSGGGG   120
SEVQLKESGP VLVKPTETLT LTCTVSGFSL TSYDISWIRQ PPGKALEWLG VIWTGGGTNY   180
NSALKSRLTI SKDNSKSQVV LTMTNMDPVD TATYYCVPHY YGYAMDYWGQ GTTVTVSS    238

SEQ ID NO: 28           moltype = DNA   length = 714
```

| FEATURE | Location/Qualifiers |
|---|---|
| misc_feature | 1..714 |
| | note = 2G1-V12 scfv |
| source | 1..714 |
| | mol_type = other DNA |
| | organism = synthetic construct |

SEQUENCE: 28

```
gagatcgtgt tgacccagag ccctgccacg ctgagcctgt cccccgggga gcgcgccact   60
ctttcgtgta gggcttccca ggacattaac aagtacatcg catggtacca gcagaagccc  120
ggacaggccc cccgcctgct catccactac acatcccacc gccagacagg catcccggct  180
cgattctctg gttctggcag cggtcgtgat tacacccttac ctatttcttc cctggagcca  240
gaggactttg cggtgtacta ctgcctgcag tatgacaacc tgctgacctt cggcggaggc  300
accaagctgg agatcaaggg cggcggtggc tccggtggag gcggatctgg cggtggcggg  360
tcggaggtgc agctgaagga gagcggggcg gtgctgaagg agcctaccgg agactctgac  420
ctgacctgca ctgtttccgg cttctctctg acgagctacg acatcagttg gatccgccag  480
ccacccggca aagcgttgga atggctcggg gtaatttgga ccggtggcgg gaccaactac  540
aacagcgcgc tcaatcgcg gctaaccatc tcaaaggaca actccaagtc ccaagtggtg  600
ttaactatga caaatatgga tccggtcgac accgctacct attactgcgt gcctcattac  660
tacggctacg ccatggatta tggggccag ggcacgaccg tgaccgtctc cagt        714
```

| | |
|---|---|
| SEQ ID NO: 29 | moltype = DNA length = 1178 |
| FEATURE | Location/Qualifiers |
| misc_feature | 1..1178 |
| | note = EF1 promoter |
| source | 1..1178 |
| | mol_type = other DNA |
| | organism = synthetic construct |

SEQUENCE: 29

```
gctccggtgc ccgtcagtgg gcagagcgca catcgcccac agtccccgag aagttggggg   60
gaggggtcgg caattgaacc ggtgcctaga aaggtgccg cggggtaaac tgggaaagtg  120
atgtcgtgta ctggctccgc cttttttcccg agggtggggg agaaccgtat ataagtgcag  180
tagtcgccgt gaacgttctt tttcgcaacg ggtttgccgc cagaacacag gtaagtgccg  240
tgtgtggttc ccgcgggcct ggcctcttta cgggttatgg cccttgcgtg ccttgaatta  300
cttccacctg gctgcagtac gtgattcttg atcccgagct tcgggttgga agtgggtggg  360
agagttcgag gccttgcgct taaggagccc cttccgctcg tgcttgagtt gaggcctggc  420
ctgggcgctg gggccgccgc gtgcgaatct ggtggcacct tcgcgcctgt ctcgctgctt  480
tcgataagtc tctagccatt taaaattttt gatgacctgc tgcgacgctt ttttctggc  540
aagatagtct tgtaaatgcg ggccaagatc tgcacactgg tatttcggtt tttggggccg  600
cgggcggcga cggggcccgt gcgtcccagc gcacatgttc ggcgaggcgg ggcctgcgag  660
cgcggccacc gagaatcgga cggggggtagt ctcaagctgg ccggcctgct ctggtgcctg  720
gcctcgcgcc gccgtgtatc gccccgccct gggcggcaag gctggcccgg tcggcaccag  780
ttgcgtgagc ggaaagatgg ccgcttccgg gccctgctgc agggagctca aaatggagga  840
cgcggcgctc ggggagacgg gcgggtgagt cacccacaca aaggaaaagg gcctttcgg  900
cctcagccgt cgcttcatgt gactccactg agtaccgggc gccgtccagg cacctcgatt  960
agttctcgag cttttggagt acgtcgtctt taggttgggg ggaggggttt tatgcgatgg 1020
agtttcccca cactgagtgg gtggagactg aagttaggcc agcttggcac ttgatgtaat 1080
tctccttgga atttgccctt tttgagtttg gatcttggtt cattctcaag cctcagacag 1140
tggttcaaag tttttttctt ccatttcagg tgtcgtga                        1178
```

| | |
|---|---|
| SEQ ID NO: 30 | moltype = DNA length = 63 |
| FEATURE | Location/Qualifiers |
| misc_feature | 1..63 |
| | note = signal peptide |
| source | 1..63 |
| | mol_type = other DNA |
| | organism = synthetic construct |

SEQUENCE: 30

```
atggccttac cagtgaccgc cttgctcctg ccgctggcct tgctgctcca cgccgccagg   60
ccg                                                                63
```

| | |
|---|---|
| SEQ ID NO: 31 | moltype = DNA length = 135 |
| FEATURE | Location/Qualifiers |
| misc_feature | 1..135 |
| | note = CD8 Hinge |
| source | 1..135 |
| | mol_type = other DNA |
| | organism = synthetic construct |

SEQUENCE: 31

```
accacgacgc cagcgccgcg accaccaaca ccggcgccca ccatcgcgtc gcagccctg    60
tccctgcgcc cagaggcgtg ccggccagcg gcggggggcg cagtgcacac gagggggctg  120
gacttcgcct gtgat                                                   135
```

| | |
|---|---|
| SEQ ID NO: 32 | moltype = DNA length = 72 |
| FEATURE | Location/Qualifiers |
| misc_feature | 1..72 |
| | note = transmembrane domain |
| source | 1..72 |
| | mol_type = other DNA |
| | organism = synthetic construct |

```
SEQUENCE: 32
atctacatct gggcgccctt ggccgggact tgtggggtcc ttctcctgtc actggttatc    60
acccttact  gc                                                        72

SEQ ID NO: 33           moltype = DNA  length = 126
FEATURE                 Location/Qualifiers
misc_feature            1..126
                        note = 4-1BB
source                  1..126
                        mol_type = other DNA
                        organism = synthetic construct
SEQUENCE: 33
aaacggggca gaaagaaact cctgtatata ttcaaacaac catttatgag accagtacaa    60
actactcaag aggaagatgg ctgtagctgc cgatttccaa agaagaagaa ggaggatgt    120
gaactg                                                              126

SEQ ID NO: 34           moltype = DNA  length = 336
FEATURE                 Location/Qualifiers
misc_feature            1..336
                        note = CD3 zeta
source                  1..336
                        mol_type = other DNA
                        organism = synthetic construct
SEQUENCE: 34
agagtgaagt tcagcaggag cgcagacgcc cccgcgtaca gcagggccaa gaaccagctc    60
tataacgaac tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat  ggcggaggcc tacagtgaga ttgggatgaa aggcgagcgc   240
cggaggggca aggggcacga tggcctttac caggtctcag gtacagccac caaggacacc   300
tacgacgccc ttcacatgca ggccctgccc cctcgc                             336

SEQ ID NO: 35           moltype = DNA  length = 591
FEATURE                 Location/Qualifiers
misc_feature            1..591
                        note = WPRE
source                  1..591
                        mol_type = other DNA
                        organism = synthetic construct
SEQUENCE: 35
atcaacctct ggattacaaa atttgtgaaa gattgactgg tattcttaac tatgttgctc    60
cttttacgct atgtggatac gctgctttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt tgctgacgca accccactg    240
gttggggcat tgccaccacc tgtcagctcc tttccgggac tttcgctttc ccctccta    300
ttgccacggc ggaactcatc gccgcctgcc ttgcccgctg ctggacaggg gctcggctgt   360
tgggcactga caattccgtg gtgttgtcgg ggaagctgac gtccttttcca tggctgctcg   420
cctgtgttgc cacctggatt ctgcgcggga cgtccttctg ctacgtcccc tcggccctca   480
atccagcgga ccttccttcc gcggcctgc  tgcggctct gcggcctctt ccgcgtcttc    540
gccttcgccc tcagacgagt cggatctccc tttgggccgc ctccccgcct g            591

SEQ ID NO: 36           moltype = AA  length = 21
FEATURE                 Location/Qualifiers
REGION                  1..21
                        note = signal peptide
source                  1..21
                        mol_type = protein
                        organism = synthetic construct
SEQUENCE: 36
MALPVTALLL PLALLLHAAR P                                              21

SEQ ID NO: 37           moltype = AA  length = 45
FEATURE                 Location/Qualifiers
REGION                  1..45
                        note = CD8 Hinge
source                  1..45
                        mol_type = protein
                        organism = synthetic construct
SEQUENCE: 37
TTTPAPRPPT PAPTIASQPL SLRPEACRPA AGGAVHTRGL DFACD                    45

SEQ ID NO: 38           moltype = AA  length = 24
FEATURE                 Location/Qualifiers
REGION                  1..24
                        note = transmembrane domain
source                  1..24
                        mol_type = protein
                        organism = synthetic construct
SEQUENCE: 38
IYIWAPLAGT CGVLLLSLVI TLYC                                           24
```

```
SEQ ID NO: 39              moltype = AA   length = 42
FEATURE                    Location/Qualifiers
REGION                     1..42
                           note = 4-1BB
source                     1..42
                           mol_type = protein
                           organism = synthetic construct
SEQUENCE: 39
KRGRKKLLYI FKQPFMRPVQ TTQEEDGCSC RFPEEEEGGC EL                    42

SEQ ID NO: 40              moltype = AA   length = 112
FEATURE                    Location/Qualifiers
REGION                     1..112
                           note = CD3 zeta
source                     1..112
                           mol_type = protein
                           organism = synthetic construct
SEQUENCE: 40
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112

SEQ ID NO: 41              moltype = AA   length = 8
FEATURE                    Location/Qualifiers
REGION                     1..8
                           note = CD19_VH_CDR1
source                     1..8
                           mol_type = protein
                           organism = synthetic construct
SEQUENCE: 41
GVSLPDYG                                                          8

SEQ ID NO: 42              moltype = AA   length = 7
FEATURE                    Location/Qualifiers
REGION                     1..7
                           note = CD19_VH_CDR2
source                     1..7
                           mol_type = protein
                           organism = synthetic construct
SEQUENCE: 42
IWGSETT                                                           7

SEQ ID NO: 43              moltype = AA   length = 14
FEATURE                    Location/Qualifiers
REGION                     1..14
                           note = CD19_VH_CDR3
source                     1..14
                           mol_type = protein
                           organism = synthetic construct
SEQUENCE: 43
AKHYYYGGSY AMDY                                                   14

SEQ ID NO: 44              moltype = AA   length = 6
FEATURE                    Location/Qualifiers
REGION                     1..6
                           note = CD19_VL_CDR1
source                     1..6
                           mol_type = protein
                           organism = synthetic construct
SEQUENCE: 44
QDISKY                                                            6

SEQ ID NO: 45              moltype =      length =
SEQUENCE: 45
000

SEQ ID NO: 46              moltype = AA   length = 9
FEATURE                    Location/Qualifiers
REGION                     1..9
                           note = CD19_VL_CDR3
source                     1..9
                           mol_type = protein
                           organism = synthetic construct
SEQUENCE: 46
QQGNTLPYT                                                         9

SEQ ID NO: 47              moltype = AA   length = 119
FEATURE                    Location/Qualifiers
REGION                     1..119
```

|  |  |
|---|---|
|  | note = CD19_VH |
| source | 1..119 |
|  | mol_type = protein |
|  | organism = synthetic construct |

SEQUENCE: 47
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVS   119

|  |  |
|---|---|
| SEQ ID NO: 48 | moltype = AA   length = 128 |
| FEATURE | Location/Qualifiers |
| REGION | 1..128 |
|  | note = CD19_VL |
| source | 1..128 |
|  | mol_type = protein |
|  | organism = synthetic construct |

SEQUENCE: 48
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEIT                                                         128

|  |  |
|---|---|
| SEQ ID NO: 49 | moltype = DNA   length = 360 |
| FEATURE | Location/Qualifiers |
| misc_feature | 1..360 |
|  | note = CD19_VH |
| source | 1..360 |
|  | mol_type = other DNA |
|  | organism = synthetic construct |

SEQUENCE: 49
tctgaggtga aactgcagga gtcaggacct ggcctggtgg cgccctcaca gagcctgtcc   60
gtcacatgca ctgtctcagg gtctcattca cccgactatg gtgtaagctg gattcgccag  120
cctccacgaa agggtctgga gtggctggga gtaatatggg gtagtgaaac cacatactat  180
aattcagctc tcaaatccag actgaccatc atcaaggaca actccaagag ccaagttttc  240
ttaaaaatga cagtctgca aactgatgac acagccattt actactgtgc caaacattat   300
tactacggtg gtagctatgc tatggactac tggggccaag gaacctcagt caccgtctcc  360

|  |  |
|---|---|
| SEQ ID NO: 50 | moltype = DNA   length = 384 |
| FEATURE | Location/Qualifiers |
| misc_feature | 1..384 |
|  | note = CD19_VL |
| source | 1..384 |
|  | mol_type = other DNA |
|  | organism = synthetic construct |

SEQUENCE: 50
atggccttac cagtgaccgc cttgctcctg ccgctggcct tgctgctcca cgccgccagg   60
ccggacatcc agatgacaca gactacatcc tccctgtctg cctctctggg agacagagtc  120
accatcagtt gcagggcaag tcaggacatt agtaaatatt taaattggta tcagcagaaa  180
ccagatggaa ctgttaaact cctgatctac catacatcca gattacactc aggagtccca  240
tcaaggttca gtggcagtgg gtctggaaca gattattctc tcaccattag caacctggag  300
caagaagata ttgccactta cttttgccaa caggtaata cgcttccgta cacgttcgga   360
gggggaccaagagctggagat caca                                        384

|  |  |
|---|---|
| SEQ ID NO: 51 | moltype = AA   length = 5 |
| FEATURE | Location/Qualifiers |
| REGION | 1..5 |
|  | note = Bi-specific CART linker |
| source | 1..5 |
|  | mol_type = protein |
|  | organism = synthetic construct |

SEQUENCE: 51
GGGGS                                                            5

|  |  |
|---|---|
| SEQ ID NO: 52 | moltype = DNA   length = 15 |
| FEATURE | Location/Qualifiers |
| misc_feature | 1..15 |
|  | note = Bi-specific CART linker |
| source | 1..15 |
|  | mol_type = other DNA |
|  | organism = synthetic construct |

SEQUENCE: 52
ggcgggggag gctct                                                 15

|  |  |
|---|---|
| SEQ ID NO: 53 | moltype = DNA   length = 15 |
| FEATURE | Location/Qualifiers |
| misc_feature | 1..15 |
|  | note = Bi-specific CART linker |
| source | 1..15 |
|  | mol_type = other DNA |
|  | organism = synthetic construct |

SEQUENCE: 53

```
ggcggagggg gctcc                                                                           15

SEQ ID NO: 54          moltype = AA   length = 18
FEATURE                Location/Qualifiers
REGION                 1..18
                       note = Bi-specific CART linker
source                 1..18
                       mol_type = protein
                       organism = synthetic construct
SEQUENCE: 54
GSTSGSGKPG SGEGSTKG                                                                        18

SEQ ID NO: 55          moltype = DNA  length = 54
FEATURE                Location/Qualifiers
misc_feature           1..54
                       note = Bi-specific CART linker
source                 1..54
                       mol_type = other DNA
                       organism = synthetic construct
SEQUENCE: 55
ggctccacca gtggttctgg gaaacctggt agtggggagg gctcgacgaa gggg                                54
```